US006476200B1

(12) United States Patent
Sabatini et al.

(10) Patent No.: US 6,476,200 B1
(45) Date of Patent: Nov. 5, 2002

(54) MAMMALIAN PROTEINS THAT BIND TO FKBP12 IN A RAPAMYCIN-DEPENDENT FASHION

(75) Inventors: David M. Sabatini, Baltimore, MD (US); Hediye Erdjument-Bromage, New York, NY (US); Mary Lui, Kew Gardens, NY (US); Paul Tempst, New York, NY (US); Solomon H. Snyder, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 08/265,967

(22) Filed: Jun. 27, 1994

(51) Int. Cl.[7] .................................................. A23J 1/00
(52) U.S. Cl. ........................ 530/413; 530/413; 435/69.1
(58) Field of Search .............................. 530/413, 350; 435/69.1

(56) References Cited

PUBLICATIONS

Cafferkey, R., et al. (1993) *Mol. Cell. Biol.* 13 (10): 6012–23.*
Kunz et al., "Cyclosporin A, FK506 and Rapamycin: More than Just Immunosuppression", *Trends in Biochemical Science*, 18(9):334–338 (1993).
Eidus et al., "A New Fixative for Molecular Biology and Diagnostic Pathology: Approximating a Universal Fixative", *FASB Journal*, 8(4):Abstract 2261 (1994).
Kunz et al., Target of Rapamycin in Yeast, TOR2, is an Essential Phosphaticylinositol Kinase Homolog Required for $G_1$ Progression, *Cell* (73):585–596 (1993).
Heitman et al., "Targets for Cell Cycle Arrest by the Immunosuppressant Rapamycin in Yeast", *Science*, 253:905–909 (1991).
Heitman et al., "Proline Isomerases at the Crossroads of Protein Folding, Signal Transduction, and Immunosuppression", *The New Biologist*, 4(5):448–460 (1992).
Standaert et al., Molecular Cloning and Overexpression of the Human FK506–Binding Protein FKBP, *Nature* 346:671–674 (1990).
Heitman et al., FK 506–Binding Protein Proline Rotamase is a Target for the Immunosuppressive Agent FK 506 in *Saccharomyces cerevisiae, Proc. Natl. Acad. Sci. USA*, 88:1948–1952 (1991).
Cantley et al., "Oncogenes and Signal Transduction", *Cell*, 64:281–302 (1991).

* cited by examiner

Primary Examiner—Rebecca E. Prouty
Assistant Examiner—Kathleen Kerr
(74) *Attorney, Agent, or Firm*—Banner & Witcoff, Ltd.

(57) ABSTRACT

A protein complex containing 245 kDa and 35 kDa components, designated RAFT1 and RAFT2 (for Rapamycin And FKBP12 Target) interacts with FKBP12 in a rapamycin-dependent manner. This interaction has the pharmacological characteristics expected from the observed in vivo effects of rapamycin: it occurs at low nanomolar concentrations of rapamycin and is competed by excess FK506. Sequences (330 amino acids total) of tryptic peptides derived from the affinity purified 245 kDa RAFT1 reveals striking homologies to the predicted products of the yeast TOR genes, which were originally identified by mutations that confer rapamycin resistance in yeast. A RAFT1 cDNA was obtained and found to encode a 289 kDa protein (2550 amino acids) that is 43% and 39% identical to TOR2 and TOR1, respectively.

2 Claims, 10 Drawing Sheets

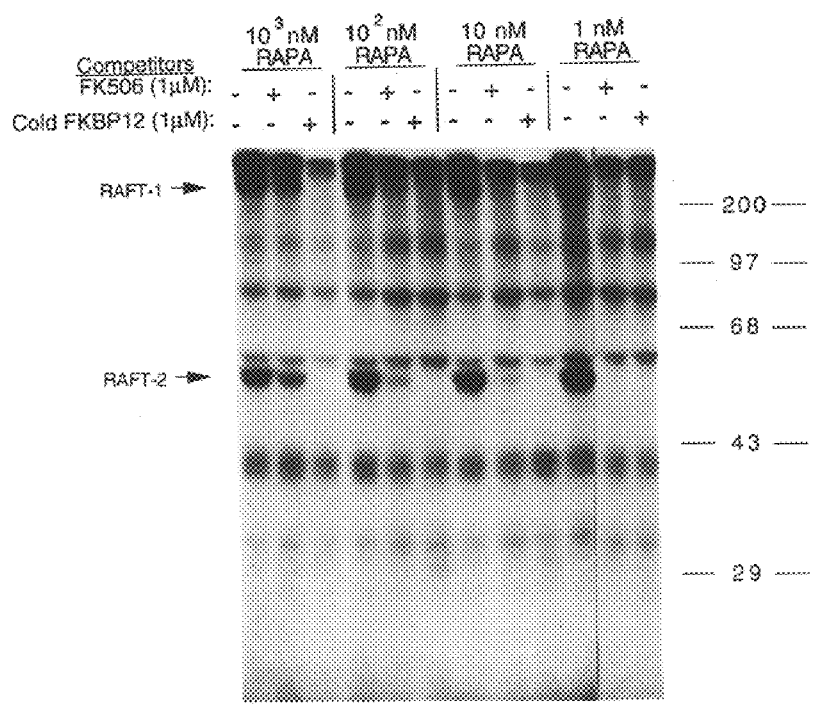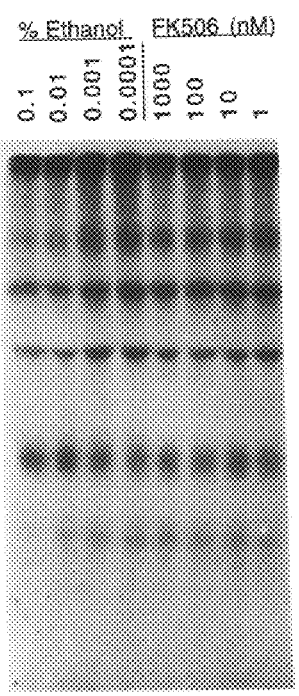

FIG. 4A

```
RAFT1  MLGTGPATATAGAATSSNVSVLQQFASGLKSRNEETRAKAAKELQHYVTME
TOR2   SAGHIGKISFVDSELDTTFSTLNLIFDKLKSDVPOERASGANELSTTLTSL
TOR1   TSSRFDGVVIGSNGDVNFKPILEKIFRELTSDYKEERKLASISLFDLLVSL

RAFT1  STRIGRFANYLRNLLPSSDPVVMEMASKAIGRLAMAGDTFTAEYVEFEVKR
TOR2   QT---SRLANYERVLIPSSDIEVMRLAANTLGRLTVPGGTLTSDFVEFEVRT
TOR1   ET---SRLAGYLERGLIPSNDVEVMRLAAKTLGKLAVPGGTYTSDFVEFEIKS

RAFT1  AVWDPKQAIREGAVAALRACLITTOREPKEMQKPOWYRHTFEEAEKGFDE
TOR2   PLRDAKLIIRLDAAVALGKCETIIQDRDPA--LGKQWFORLFQGCTHGLS-
TOR1   ALRDPHLVIRIDASITLEAKCLSTLRNRDPQ---LTSQWVQRLATSCEYGFQ-

RAFT1  DLMGFGTKPRHITPFTSFQAVQPQQSNALVGLLGYSSHQGLMGFGASPSPT
TOR2   --------------------------------------------------
TOR1   --------------------------------------------------

RAFT1  FTDTQVLQDTMNHVLSCVKKEKER-------------TAAFQALGL
TOR2   FTK-KYLDRIMVHYER------YLKNIDMNAANNSDKPFILVSIGD
TOR1   FAG-KYLEHQIMDNYLEEILTNAPAKKIPHLKD------DKPOILISIGD

RAFT1  GPGIOODI-KELLEPMLEAVGLSPALTAVLYDESRQIPQLKKDIQDGLKME
TOR2   GPAFAKHLNKDLLNLMENCPMSDHMQETLMILNEKIPSLESTVNSRILNLE
TOR1   GPVLGKLLNRNIUDLMFKCPLSDYMOETFQILETERIPSLGPKINDELLNLV

RAFT1  SDVASITLALRTLGSFEFEGHSLTQFEVRHCADHFLNSEHKEIRMEAARTCS
TOR2   TDAQILIQCFKMLQLIHHQ-YSLTEEVRLITISYIEHEDSSVRKLAALTSC
TOR1   NDIKIDIQAFRMLEKNIKSR-FSLVEFVRIVALSYIEHTDPRVRKLAALTSC

RAFT1  LDERFDAHLAOAENLOALFVALNDOVFEIRELAICTVGRLSSMNPAFVMPF
TOR2   LGSNFDPQLAQPDNLERLLFMALNDEIFGIOLEAIKIIGRLSSVNPAYVVPS
TOR1   LNPCFDPQLAQPDNLERLLFTALHDESFNIQSVAMELVGRLSSVNPAYYIPS

RAFT1  KDPDPDPNPGVINNVLATIGELAQVSGLEMRKWVDELFVIIMDMLQDSLL
TOR2   Q----DASSAVASTALKVLGELSVVGGKEMTRYLKELMPLIJNTFQDOSNS
TOR1   Q-----DTSSTVASTALRTIGELSVVGGEDMKIYLKDLFPLIJIKTFQDOSNS
```

FIG. 4B

```
LREMSQEESTRFYDQLNHHIFELVSSSDANERKGGILAIASLIGV----EGGN    100
AREVSAEQFQRFSNSLNNKIFELIHGFTSSEKIGGILAVDTLISFYLSTEELPN   169
EHELSIEEFQAISNDINNKILELVHTKKTNTRVGAVESIDTLISFYAYTERLPN   157

ALEWL--GADRN-------EGRRHAAVLVLRELAISVPTFFQQVQPFFDNIFV    196
CIDWLTLTADNNS-SSSKLEYRRHAALLIIKALADNSPYLLYPYVNSILDNIWV   271
CLEWLTASTEKNSFSSSKPDHAKHAALLIITALAENCPYLLYQYLNSILDNIWR   260

TLAKEKGMNRDDRIHGALLILNELVRISSMEGERLREEMEEITQQQLVHDKYCK   301
-------LNTNDSVHATLLVFRELLSLKA----------------------    350
-------VNTLECTHASLLVYKEILFLKD----------------------    339

KSTLVESRCCRDLMEEKEDQVCQWVLKCRSSKNSLIQMTILNLLPRLVAFRPSA   406
-------PYLRDKYDDIYKSTMKYKEYKFDVIRREVYAILPLLAAFDRAI      384
-------PFLNQVEDQMCLNCIAYENHKAKMIREKIYQIVPLLASFNRQL       373

LSVAVRSEFKVVLPRVLDIIRAALPPKDFAHKRQKTVQVDATVFTCISMLARAM  493
IAFEVGSSISPYMTLIEDNIREGERTK-FKVRKO----FEKDLFYCIGKLACAL  472
IAYEVGPDIAPYVKQILDYIEHDLQTK-FKFRKK----FENEIFYCIGRLAVPL  463

SLVLMHKPLRHPGMPK-----------------------GLAHQLASPGLTTLPEA  576
SISLSGEKFIQ--------SNQYDFNNOFSIEKARKSRNQSFMKKTGESN-DDI    568
CSTLSGTRFIQPGSRMEIPS--------FSRERAREWRNKSILQKTGESN-DDN   559

RELTPSIHLISGHAHVVSQTAVQV---VADVLSKLLVVGITDPDPDIRYCVLAS   678
DLFI------KDDICKQTSVHALHSVSEVLSKLLEMIAITDPVAEIRLEILQH   664
EIYV------KDNICKQTSLHSLNTVSEVLSKLLEAITIADPLODIRLEYLKN   655

LRKMLIQILTELEHSGIGRIKEQSARMLGHLVSNAPRLIRPYMEPIEKALILKL   783
LRKTLELELLTQLKFSNMPKKKEESATLLCTLINSSDEVAKPYIDPILDVILPKC   769
IRKILLELLTKLKFSTSSREKEETASLLCTLIRSSKDVAKPYIEPLLNVLLPKF   760

AKRQVALWTLGQLVASTGYVVEPYRKYPTLLEVLLNFLKTEQNQGTRREAIRVL   888
FKRDAALTILGQLAASSGYVVGPLLDYPELLGILINILKTENNPHIRRGTVRLI   870
FKREAALKALGQLAASSGYVIDPLLDYPELLGILVNILKTENSQNIRRQTVTLI  861
```

FIG. 4C

```
RAFT1  GILGAIDPYKHKVNIGMIDOSRDASAVSLSESKSSQDSSDYSTSEMLVNMG
TOR2   GILGAIDPYKHR------EIEVT----SNSKSSVEQNAPSIDIALLMQG
TOR1   GILGAIDPYRQK------EREVT----STTDISTEQNAPPIDIALLMQG

RAFT1  VMPTFLNVIRVCDGAIREFLFQQLGMLVSFVKSHIRPYMDEIVTLMREFWV
TOR2   IIPGIILVMRSCPPSQLDFYFQQLGSLISIVKQHIRPHVEKIYGVIREFFP
TOR1   IIPTIEDVMRTCSQSLLEFYFQQLCSLIIIVRQHIRPHVDSIFQAIKDFSS

RAFT1  AAIQLFGANLDDYLHLLLPPIVKLFDAPEVPLPSRKAALETVDRLTESLDF
TOR2   KSLVTFGPNLEDYSHLIMPIVYRMTEYSAGSL--KKISIITLGRLAKNINL
TOR1   RLLESFGPNLEGYSHLITPKIVQMAEFTSGNL--QRSAIITIGKLAKDVDL

RAFT1  RHRINHQRYDVEICRIVKGYTLA------DEEEDPLIYQHRMLRSSQGD
TOR2   RNRIQHSVYDQLVNKLLNNECLPTNIIFDKENEVPERKNYEDEMQ-----
TOR1   KKHIQHTIYDDLTNRILNNDVLPTKIL---EANTTDYKPAE--QMEAADAG-

RAFT1  PSLRSCWALAQAYNPMARDLFNAAFVSCWSEENEDOODELIRSIELAITS-
TOR2   ACLRSCSSLVSVYYPLARELENASFSSSCWVELQTSYQEDLIQALCKALSSS
TOR1   HALRACSNLASMYYPLAKELENTAFACVWTELYSQYQEDLIGSLCIALSSP

RAFT1  LEFQKGPTPAILESLISINNKLOOPEAASGVLEYAMKHFGELEIQATWYEK
TOR2   VEFLEEPKNSTIEALISINNQLHQTDSAIGIEKHAQOH-NELQLKETWYEK
TOR1   IKFIKEPENSTIESLISINNQLNQTDAAIGILKHAQOH-HSLQLKETWFEK

RAFT1  ETQAKMARMAAAAAWGLGQWDSMEEYTCMIPRDTHDGAFYRAVLAHQDLF
TOR2   EVKKAMAPLAAGAAWGLEQWDEIAQYTSVMKSQSPDKEFYDAILCLHRNNF
TOR1   QTKKLIAPLAAGARWGLEGEWDMLEQYISVMKPKSPDKEFFDAILYLHKNDY

RAFT1  -ERREIIRQIWWERLQGCORIVEDWQKILMVRSLVVSPHEDMRTWLKYASL
TOR2   SDKRLTMRETWNTRLLGCQKNIDVWQRILRVRSLVIKPKEDAQVRIKFANL
TOR1   SEKKLHYQNLWTKRLLGCQKNVDLWQRVLRVRSLVIKPKQDLQIWIKFANL

RAFT1  IDAFQHMQHF--------VQTMQQQAQHAIATEDQOHKQELHK
TOR2   DEALKQLINFTSRMAHDLGLDPNNMIAQSVPQQSKRV----PRHVEDYTK
TOR1   KEALNHLIGETSRLAHDLGLDPNNMIAQSVKLSSAST----APYVEEYTK
```

FIG. 4D

```
NLPL-DEFYPAVSMVALMRIFRDQSLSHHHTMVVQAITFIFKSLGLKCVQFLPQ      992
VSPSNDEYYLTVVIHNLMKILNDPSLSIHHTAAIQAIMHIFQNLGLRCVSFLDQ      963
MSPSNDEYYTTVVIHCLLKILKDPSLSSYHTAVIQAIMHIFQTLGLKCVSFLDQ      954

MNTSIQSTILLLIEQIVVALGGEFKLYLPQLIPHMLRVFMHDNSQGRIVSIKLL     1097
I-IKLQITIISVIESISKALEGEFKRFVPETLTFFLDILENDQSNKRIVPIRIL     1067
V-AKLQITLVSVIEAISKALEGEFKRLVPLTLTFLVILENDKSSDKVLSRRVL      1058

TDYASRIIHPIVRTLDQ--SPELRSTAMDTLSSLVFQLGKKYQIFIPMVNKVLV     1200
SEMSSRIVQALVRILNNGDR-ELTKATMNTLSLLLQLGTDFVVFVPVINKALL      1169
FEMSSRIVHSLLRVLSSTTSDELSKVIMNTLSLLLIQMGTSFAIFIPVINEVLM     1161

ALASGPVETGPMKKLHVSTINLQKAWGAARRVSKDDWLEWLRRLSLELLKDSSS     1297
--------VTKLEPVNONILKNAWYCSQOKTKEDWQEWIRRLSIOLLKESPS      1257
--------VAKLEPINQSVLKSAWNSSQORTKEDWQEWSKRLSIQLLKESPS      1250

QDIAEVTQTLLENLAEFMEHSDKGPLEPLRDDNGJVLLGERAAKCRAYAKALHYKE    1401
ENPPEIYQMLLENLEVEFMEHDDK--PLPIP----IHTLGKYAQKCHAFAKALHYKE   1357
LNPPEIHQTLLENLEVEFMEHDDK-ALPIP----TQSLGEYAERCHAYAKALHYKE    1350

LHEWEDALVAYDKKMDTNKDDPELMLGRMRCLEALGEWGQLHQQCCEKWTLVND     1506
LQRWEDALAAYNEKEAAGEDSVEVHMGKLRSLYALGEWEELSKLASEKWGTAKP      1461
LERWEDALIHAYNEREKAGDTSVSVTLGKMRSLHALGEWEQLSQLAARKWKVSKL     1454

SLAQQCIDKARDLLDAEETAMAGESYSRAYGAMVSCHMLSELEEVIQYKLVP--     1609
KKAEVHIFNARDLLVTELESALVNESYNRAYNVVVRAQIIAELEEIIKYKKLPQN     1566
DNASKHILNARDLLVTEISALINESYNRAYSVIVRTQIITEFEEIIKYKQLPPN     1559

CGKSGRLALAHKTLVLLE--GVDPSRQLDHP-LPTVHPQVTYAYMKNMWKSARK     1710
CRKSGRMALAKKVLNTLLEETDDP----DHPNTAKASPPVVYAQLKYLWATGLQ      1667
CRKSGRMRLANKALNMLLEGGNDP----SLPNTVKAPPPVVYAQLKYIWATGAY     1660

LMARCFLKLGEWOLNLQGINESTIPK-VLQYYSAATEHDRSWYKAWHAWAVMNF     1798
LLARCFLKOGEWRVCLQPKWRLSNPDSILGSYLLATHFDNTWYKAWHNWALANF     1767
LLARCFLKOGEWRIATOPNWRNTNPDAILGSYLLATHFDKNWYKAWHNWALANF     1760
```

FIG. 4E

```
RAFT1  EAVLHYKHQNQARDEKKKLRHASGANITNATTTATTAASAAAATSTEGSNS
TOR2   EVISMLTSVSK---KKQE----------GSDASSVIDIN-EFDNGMIGVNT
TOR1   EVISMVQEETKLNGGKND---------DDDDTAVNNDNVRIDGSILGSGS

RAFT1  LRVLTLWFDYGHWPDVNEALVEGVKAIQIDTWLQVIPQLIARIDTPRPLVG
TOR2   ERLLTLWFTFGGIPEATQAMHEGFNLIQIGTWLEVLPQLISRIHQPNQIVS
TOR1   ERLLTLLFNFGGIKEVSQAMYEGFNLMKIENWLEVLPQLISRIHQPDPTVS

RAFT1  AMMVSEELIRVAILWHEMWHEGLEEASRLYFGERNVKGMFEVLEPLHAMME
TOR2   AELVSHELIRMAVLWHEQWYEGLDDASRQFFGEHNTEKMFAALEPLYEMLK
TOR1   AELVSHELIRVAVLWHELWYEGLEDASRQFFVEHNIEKMFSTLEPLHKHLG

RAFT1  QLPQLTSLELQYVSPKLLMCRDEELAVPGTYDPN-QPIIRIQSIAPSLQVI
TOR2   QLPQLQTLELQHVSPKLLSAHDEELAVPGTRASGGKPIVKISKFEPVFSVI
TOR1   QIPQLQTLEDLQHVSPQLLATHDLEELAVPGTYFP-GKPTIRIAKFEPLFSVI

RAFT1  KNLSIQRYAVIPLSTNSGLIGWVPHCDTLHALIRDYREKKKILLNIEHRIM
TOR2   RHLDIQQYPAIPLSPKSGLLGWVPNSDTFHVLIREHREAKKIPLNIEHWVM
TOR1   RHLDIQQYPAIPLSPKSGLLGWVPNSDTFHVLIREHRDAKKIPLNIEQVVM

RAFT1  SLAVMSMVGYILGLGDRHPSNLMLDRLSGKILHIDFGDCFEVAMTREKFPE
TOR2   SLAVMSMTGYILGLGDRHPSNLMLDRITGKVIHIDFGDCFEAAILREKFPE
TOR1   SLAVMSMTGYILGLGDRHPSNLMLDRITGKVIHIDFGDCFEAAILREKYPE

RAFT1  NWRLMDTNAKGNKRSRTRTDSYSAGQSVEILDGVELGEPAHK---KTGTTV
TOR2   NW----------------------------------GFDL--PTKKIEEETGIQL
TOR1   HW----------------------------------GFDL--PPQKLTEQTGIPL

RAFT1  DTLDVPTQVELLIKQATSHENLCQCYIGWCPFW
TOR2   NDLDVPEQVDKLIQQATSVENLCQHYIGWCPFW
TOR1   NELDVPEQVDKLIQQATSIERLCQHYIGWCPFW
```

FIG. 4F

```
ESEAESNESSPTPSPLQKKVTEDLSKTLLLYTVPAVQGFFRSISLSRGNNLQDT   1903
---FDAKEVHYSSNLIHRHV--------IPAIKGFFHSISLSESSSLQDA      1843
---LTINGNRYPLELIQRHV--------VPAIKGFFHSISLLETSCLQDT      1840

RLIHQLLTDIGRYHPOALIYPLTVASKSTTTARHNAANKILKNMCEHSNTLVQQ  2008
RSLLSLLSDLGKAHPOALVYPLMVAIKSESLSRQKAALSIIEKMRIHSPVLVDQ  1948
NSLLSLLSDLGKAHPOALVYPLTVAIKSESVSRQKAALSIIEKIRIHSPVLVNQ  1945

RGPQTLKETSFNQAYGRDLMEAQEWCRKYMKSGNVKDLTQAWDLYYHVFRRISK  2113
RGPETLREISFQNSFGRDLLNDAYEWLMNYKKSKDVSNLNQAWDIYYNVFRKIGK 2053
NEPQTLSEVSFQKSFGRDLLNDAYEWLNNYKKSKDINNLNQAWDIYYNVFRKITR 2050

TSKORPRKLTLMGSNGHEFVFLLKGHEDLRQDERVMQLFGLVNTLLEANDPTSLR 2217
SSKORPRKFCIKGSDGKDYKYVLKGHEDIRQDSLVMQLFGLVNTLLQNDAECFR  2158
SSKORPRKFSIKGSDGKDYKYVLKGHEDIRQDSLVMQLFGLVNTLLKNDSECFK  2154

LRMAPDYDHLTLMOKVEVFEHAVNNTAGDDLEAKLLWLKSPSSEVWFDRRTNYTR 2322
LQMAPDYDNLTLLQKVEVFTYALNNTEGODLYKVLWLKSRSSETWLERRTTYTR  2263
LQMAPDYENLTLELQKIEVFTYALDNTKGODLYKILWLKSRSSETWLERRTTYTR 2259

KIPFRLTRMLTNAMEVTGLDRNYRTTCHTVMEVLEREHKDSVMAVLEAFVYDPLL 2427
KVPFRLTRMLTYAMEVSGIEGSFRITCENVMKVLRDNKGSLMAILEAFAFDPLI  2368
KVPFRLTRMLTYAMEVSGIEGSFRITCENVMRVLRDNKESLMAILEAFALDPLI  2364

PE-SIHSFIGDGLVKPEAL--------NKKAIOIINRVRDKLTGRDFSHD      2517
PVMNANELLSNGAITEEEVQRVENEHKNAIRNARAMLVLKRITDKLTGNDIRRF  2441
PLINPSELLRKGAITVEEAANMEAEQONETRNARAMLVLRRITDKLTGNDIKRF  2437

2550
                                                         2474
                                                         2470
```

MAMMALIAN PROTEINS THAT BIND TO FKBP12 IN A RAPAMYCIN-DEPENDENT FASHION

This invention was made with government support under MH18501, DA00266, and DA00074, awarded by the National Institutes of Health. The government has certain rights in this invention.

BACKGROUND OF THE INVENTION

The natural products cyclosporin A, FK506, and rapamycin are potent immunosuppressants with realized or potential clinical applications in the prevention of graft rejection after organ transplantation and the treatment of autoimmune disorders (Borel, 1986; Kino et al., 1987; Martel et al., 1977). These drugs act by inhibiting intermediate steps in the signaling pathways that effect the T-cell response to antigen (for reviews see, Fruman et al., 1994; Kunz and Hall, 1993; Liu, 1993; Schreiber, 1991). This makes them useful probes for identifying the components of those pathways and determining their physiological roles.

The immunosuppressants interact with the immunophilins, which are small, soluble, receptor proteins that mediate their actions. Cyclosporin A (a cyclical undecapeptide) binds to cyclophilin A, whereas FK506 and rapamycin (two related macrolide antibiotics) bind to a distinct receptor protein, FKBP12 (Handschumacher et al., 1984; Harding et al., 1989; Siekierka et al., 1989). Though cyclophilin and FKBP12 differ markedly in amino acid sequence, both immunophilins have peplidyl-prolyl cis-trans isomerization (rotamase) activity, which is inhibited by their respective ligands (for review, see Heitman et al., 1992). However, this inhibition does not appear to explain the effects of the immunosuppressants (Bierer et al., 1990a, b; Tropschug et al., 1989). Instead, the action of cyclosporin A and FK506 derives from the binding of the drug-receptor complexes to the calcium-activated protein phosphatase, calcineurin (Liu et al., 1991). This association inhibits the catalytic activity of the phosphatase, which is required for the $Ca^{++}$-dependent initial step in the activation of the T-lymphocyte via the T-cell receptor (Flanagan et al., 1991; Kronke et al., 1984).

On the other hand, rapamycin appears to block a later, $Ca^{++}$-independent stage in the T-cell response. This drug selectively inhibits the IL-2 stimulated G1 to S cell-cycle transition that initiates T-cell proliferation (Dumont et al., 1990b). Although this inhibition has been correlated with the decreased activity of the 70 kDa S6 kinase ($pp70^{S6K}$), a known downstream effector of the IL-2 receptor, the FKBP12-rapamycin complex does not appear to interact directly with this kinase (Chung et al., 1992; Kuo et al., 1992). Similarly, in T-cells and other cell types, rapamycin blocks progression of the cell cycle by preventing the activation of the cyclin-dependent kinases $p33^{cdk2}$ and $p34^{cdc2}$, but an association of the drug-immunophilin complex with the kinases or their respective cyclins has not been demonstrated (Albers et al., 1993; Jayaraman and Marks, 1993; Morice et al., 1993).

In the budding yeast S. cerevisiae, rapamycin also causes an arrest in the G1 phase of the cell cycle through its binding to a highly conserved FKBP12 homologue (Heitman et al., 1991b). The toxicity of the drug for yeast cells has allowed, through genetic selection, the identification of two homologous genes, which, when mutated, render the cells rapamycin-resistant (Heitman et al., 1991a). This led to the proposal that the products of these genes, which show some amino acid homology to the catalytic domain of the p110 subunit of PI-3 kinase, are the Targets Of Rapamycin and hence to the designation of the genes as TOR1 and TOR2 (Kunz et al., 1993). Direct support for this proposal, however, has not been presented and how the TOR gene products confer sensitivity to rapamycin remains to be elucidated. Alternatively, it has been suggested that in the signaling pathway blocked by rapamycin, the TOR proteins, like the S6 kinase and the cyclin-dependent kinases, lie downstream from the direct target of the FKBP12-rapamycin complex (Albers et al., 1993; Helliwell et al., 1994). This model assumes that the TOR mutations lead to the constitutive activation of the TOR1 and TOR2 proteins.

Besides binding to calcineurin in a FK506-dependent manner, FKBP12 can also interact with calcium-channel proteins, the ryanodine receptor, which mediates calcium induced calcium released (Jayaraman et al., 1992; Timerman et al., 1993) and the inositol 1,4,5,-triphosphate ($IP_3$) receptor (A. Cameron, A. Kaplin, D. Sabatini, J. Steiner, S. Snyder, unpublished). These associations do not require FK506 or rapamycin; indeed these drugs dissociate the FKBP12-channel complex.

There is a need in the art to identify, isolate, and purify the mammalian cellular proteins that interact with FKBP12 only in the presence of rapamycin. Such proteins play a role in immunological, neurological, and cell cycle functions.

SUMMARY OF THE INVENTION

It is an object of the invention to provide isolated, purified cDNA molecules encoding rapamycin and FKBP target molecules.

It is another object of the invention to provide fusion proteins comprising rapamycin and FKBP targets.

It is still another object of the invention to provide an isolated and purified rapamycin and FKBP target molecule.

It is still another object of the invention to provide an expression construct which directs synthesis in a cell of an RNA molecule which inibits expression of a rapamycin and FKBP target molecule.

It is yet another object of the invention to provide isolated, purified cDNA molecules which are complementary to genes encoding rapamcyin and FKBP target molecules.

It is an object of the invention to provide a method of screening for potential therapeutic agents.

It is another object of the invention to provide a method of purifying a rapamycin and FKBP target molecule.

It is still another object of the invention to provide a method of isolating DNA sequences which code for rapamycin and FKBP target molecules.

These and other objects of the inveniton are provided by one or more of the embodiments described below. In one embodiment of the invention an isolated, purified cDNA molecule is provided which encodes RAFT1, a protein having the amino acid sequence shown in SEQ ID NO:1.

In another embodiment of the invention a fusion protein comprising the amino acid sequence shown in SEQ ID NO:1, is provided.

In yet another embodiment of the invention an isolated and purified RAFT1 protein having the amino acid sequence shown in SEQ ID NO:1 is provided. Also provided is an isolated and purified RAFT2 protein, having an apparent molecular weight on SDS polyacrylamide gels of 35 kDa. Also provided is an isolated and purified mammalian RAFT protein which is free of proteins which do not bind to rapamycin and FKBP12. Also provided is a mammalian RAFT protein prepared by the process of:

contacting a preparation of mammalian proteins with FKBP12 in the presence of rapamycin;

isolating mammalian proteins which bind to FKBP12 in the presence of rapamycin from those mammalian proteins which do not bind; and dissociating bound mammalian proteins from FKBP12 to provide a mammalian RAFT protein.

In still another embodiment of the invention an expression construct is provided. The expression construct comprises a promoter operably linked to at least 20 nucleotides of the antisense strand of RAFT1 cDNA, said expression construct directing synthesis in a cell of an RNA molecule which is complementary to RAFT1 RNA.

In another embodiment of the invention an isolated, purified cDNA molecule comprising at least 20 nucleotides of the sequence of RAFT1 is provided.

In yet another embodiment of the invention a method of screening substances for potential as therapeutic agents is provided. The method comprises the steps of:

contacting a substance to be tested with three components: (a) FKBP12, (b) rapamycin, and (c) a protein selected from the group consisting of RAFT1 and RAFT2;

determining the amount of one of said components bound to the other components in the presence and absence of said substance; a substance which increases or decreases the amount of said component bound being a potential therapeutic agent.

In one embodiment of the invention a method of purifying a mammalian RAFT protein is provided. The method comprises the steps of:

contacting a preparation of mammalian proteins with FKBP12 in the presence of rapamycin;

isolating mammalian proteins which bind to FKBP12 in the presence of rapamycin from those mammalian proteins which do not bind;

dissociating bound mammalian proteins from FKBP12 to provide a mammalian RAFT protein.

In another embodiment of the invention methods of isolating mammalian RAFT DNA sequences are provided. One of the methods comprises:

probing a library of mammalian DNA sequences with a probe which comprises at least 15 contiguous nucleotides selected from the sequence of RAFT1 cDNA.

Another of the methods comprises:

amplifying a DNA sequence using at least one primer which comprises at least 10 contiguous nucleotides selected from the sequence of RAFT1 cDNA.

These and other embodiments of the invention provide the art with potent tools for identifying drugs useful in the treatment of immunological, neurological, and cell cycle-related diseases and defects.

A cytosolic fraction prepared from a rat brain homogenate was applied to a heparin column. The material that remained bound to the column after washing with 5 column volumes of wash buffer containing 200 mM KCl, was eluted with a linear gradient from 200 mM to 600 mM KCl in homogenization buffer. Aliquots of the crude cytosol (S), the column flow through (FT), and the wash (W) were tested in the crosslinking assay with (+) or without (−) rapamycin (100 nM). Every other fraction eluted from the heparin column was tested in the crosslinking assay in the presence of 100 nM rapamycin. No rapamycin specific crosslinked products are visible in the crude cytosol because of the high concentrations of endogenous FKBP12 present in the initial sample.

FIG. 2 shows FK506 and unlabeled FKBP12 prevent the rapamycin-dependent association of $^{32}$P-FKBP12 to the target proteins.

FIG. 2A) The heparin column eluate containing the RAFTs was tested in the crosslinking assay at the indicated concentrations of rapamycin with or without the addition of 1 μM FK506 or 1 μM FKBP12. FIG. 2B) Neither FK506 alone nor the ethanol vehicle induce crosslinking of FKBP12 to RAFT. The heparin eluate containing RAFT was tested in the crosslinking assay with the indicated concentrations of FK506 or ethanol. This experiment was repeated twice with identical results.

Figure 3:
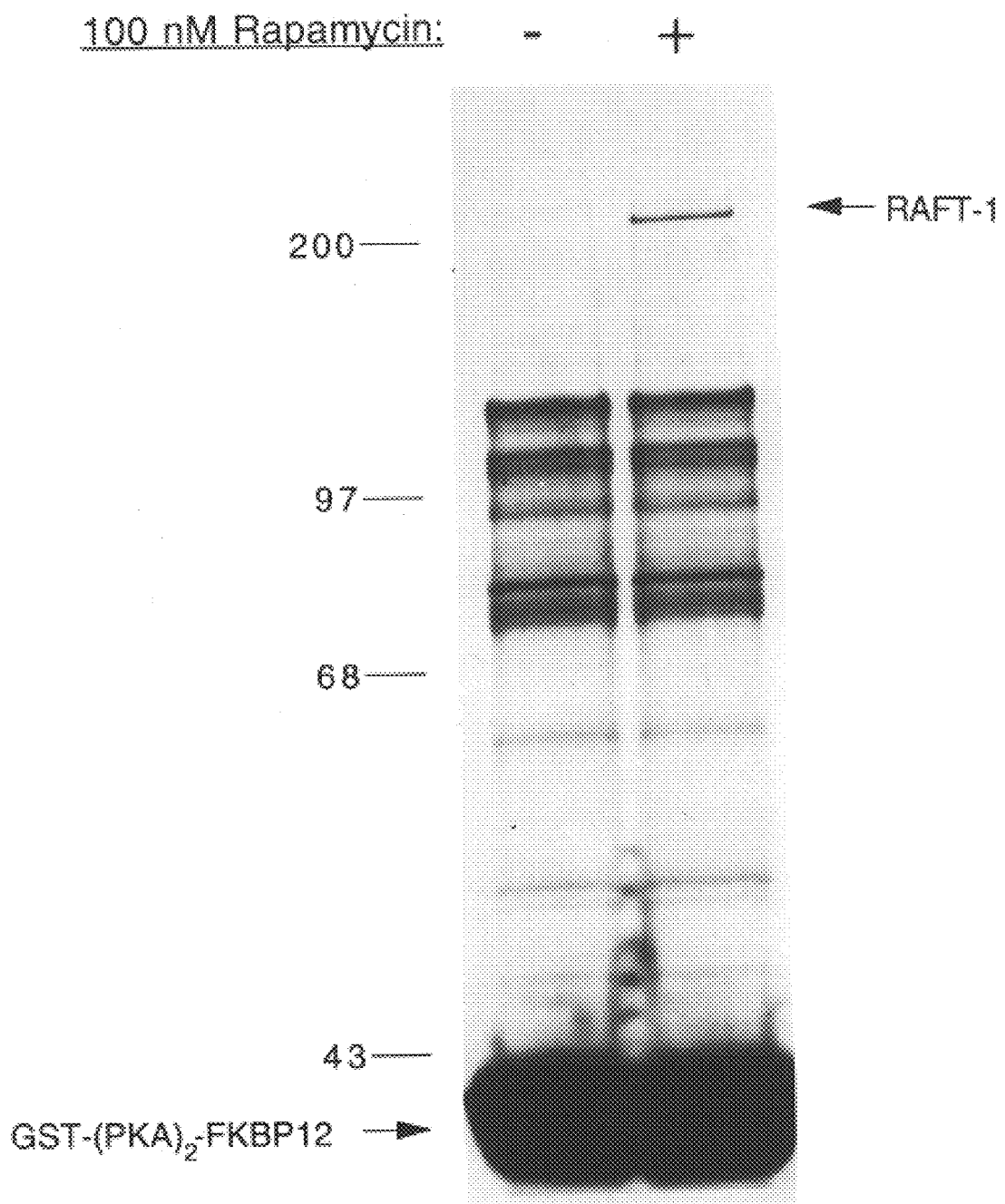

FIG. 3 shows purification of RAFT1 with a FKBP12-rapamycin affinity column.

RAFT enriched fractions eluting from the heparin column between 300 and 450 mM KCl, were incubated in the presence (+) or absence (−) of 100 nM rapamycin with GST-(PKA)2-FKBP12 fusion protein (20 μg) immobilized on glutathione agarose beads. The material that remained associated with the beads after extensive washes was analyzed by SDS-PAGE (8%) and silver staining. RAFT1 is present only in the sample treated with rapamycin. The large band at 36 kDa is the GST-FKBP12 fusion protein.

FIGS. 4A through 4F shows alignment of RAFT1 amino acid sequence (SEQ ID NO:1) with the predicted amino acid sequences of TOR2 (SEQ ID NO:3) and TOR1 (SEQ ID NO:2).

The alignment was maximized by introducing insertions marked by dashes. Sequences in RAFT1 identical to TOR2 and/or TOR1 are indicated with gray shading. The sequences of tryptic peptides obtained by microsequencing are indicated with a line above the RAFT1 sequence. Sequences used to design primers for PCR are indicated with an arrow above the residues (direction indicate sense or antisense). The PKC site conserved between RAFT1, TOR1 and TOR2 is boxed.

Figure 5:
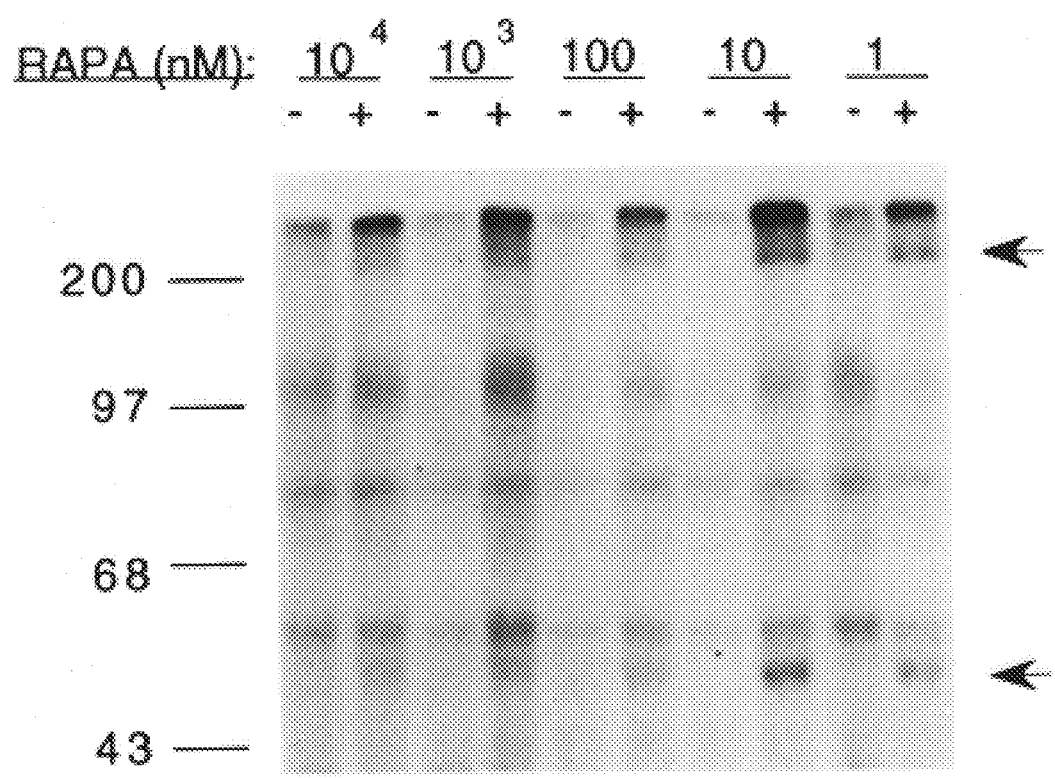

FIG. 5 shows rapamycin-dependent crosslinking of FKBP12 to two PC12 cell cytosolic proteins of approximate molecular weight 245 kDa and 35 kDa.

$^{32}$P-labeled FKBP12 ($10^5$ cpm) was incubated with cytosolic fractions from PC12 cells with or without the indicated concentration of rapamycin for 1 hr. at 4° C. The crosslinker DSS was then added and the incubation continued for 40 minutes before processing for SDS-PAGE (4%–12% gradient) and autoradiography. The arrows indicate the two bands that appear only in the presence of rapamycin. This experiment was repeated three times with identical results.

DETAILED DESCRIPTION OF THE PREFERRED EMBODIMENTS

We have isolated and identified proteins, which we designate RAFT1 and RAFT2, that interact with the FKBP12-rapamycin complex. Rapamycin-induced binding of FKBP12 to RAFT1 occurs at drug concentrations as low as 1 and 10 nM, resembling pharmacological potency in vivo (Bierer et al., 1990a; Dumont et al., 1990a). FK506 and rapamycin bind with similar affinities to the same binding site on FKBP12 and antagonize each others' actions in vivo (Bierer et al., 1990a; Dumont et al., 1990b). Consistent with these facts, FK506 does not induce interactions between FKBP12 and RAFT1 but, instead, prevents the rapamycin-mediated effect. Since rapamycin has pleiotropic effects on a wide variety of cell types, the target of its complex with FKBP12 is likely to be an early participant in several signal transduction pathways.

We have also isolated and purified a cDNA molecule which encodes RAFT1. The predicted amino acid sequence of the protein, which exactly corresponds to the empirically determined amino acid sequences of tryptic peptides of RAFT1, is shown in SEQ ID NO:1. The cDNA sequence can be used to express in recombinant cells RAFT1 proteins or portions of the RAFT1 protein. Similarly, the cDNA sequence can be used to construct fused genes which will express fusion proteins comprising all or part of the RAFT1 sequence. Having provided the art with the amino acid sequence of the RAFT1 protein, other coding sequences can be devised which differ from that isolated virtue of the degeneracy, of the genetic code. Such nucleotide sequences are within the scope of the present invention.

RAFT1 has an apparent molecular weight on SDS polyacrylamide gels of 245 kDa. RAFT2 has an apparent molecular weight on SDS polyacrylamide gels of 35 kDa. Isolated and purified RAFT1 protein can be obtained by means of recombinant DNA technology or by isolating and purifying the protein directly from natural sources. One means of purifying RAFTs involves contacting a preparation of mammalian proteins with FKBP12 in the presence of rapamycin. Those proteins which bind to FKBP12 in the presence of rapamycin can then be separated from those which do not bind. Bound proteins can then be dissociated to yield a preparation of a RAFT protein. It is convenient if the FKBP12 is immobilized, for example, on a solid support. One convenient means is to immobilize FKBP12 on a column-packing matrix. For example, an FKPB12-glutathione-S-transferase fusion protein can be readily bound to glutathione-agarose to provide immobilized FKBP12. Another means of purifying RAFT proteins is by use of a heparin chromatography column. The RAFT proteins bind to the heparin and can be eluted at 300 to 450 mM KCl.

Because of the role of rapamycin in immunological, cell cycle, and neurological functions, it may be desirable to inhibit the expression of RAFT1. One means to accomplish this is to use antisense polynucleotides. Antisense polynucleotides can be made synthetically. Alternatively, expression constructs may be used which comprise a promoter operably linked to at least 20 nucloetides of the antisense strand of RAFT1 cDNA. The expression construct directs the synthesis in a cell of an RNA molecule which is complementary to RAFT1 mRNA. Any suitable promoter can be used, depending on the cell system in which expression of the antisense molecule is desired.

The nucleotide sequence of RAFT1 can be used to generate probes which comprise at least 15–20 nucleotides of the recited sequence. These probes can be used to screen a library of mammalian DNA molecules. Techniques for making nucleotide probes and screening genomic or cDNA libraries are well known in the art. Alternatively, other RAFT nucleotide sequences can be obtained by amplification of mammalian DNA using as primers one or two polynucleotides comprising at least 10 contiguous nucleotides selected from the sequence of RAFT1. Techniques for amplification of DNA are also well known in the art.

RAFT1 and RAFT2 can be used to screen substances for potential as therapeutic agents for immunological, cell cycle, and neurological disease states. As described here, rapamycin, FKBP12, RAFT1, and RAFT2 bind to each other and form a complex. Test compounds can be screened for potential therapeutic utility by contacting a test compound with three components: (a) FKBP12; (b) rapamycin; and (c) a protein selected from the group consisting of RAFT1 and RAFT2. The amount of one of the components in the complex is determined, in the presence and in the absence of the substance to be tested. A substance which increases or decreasees the amount of the component in the complex is a potential therapeutic agent. Means used for determining amounts of components can be any known in the art, including the use of radioactive components, antibodies specific for components, densitometry, etc.

EXAMPLES

The following materials were used in the examples described below. Frozen rat brains stripped of the meninges were obtained from Harlan Bioproducts (Indianapolis, Ind.). Other materials were purchased from the following sources: [$\gamma$-$^{32}$P]-ATP (NEG-02z) from New England Nuclear (Cambridge, Mass.), glutathione-agarose, heart muscle kinase (PKA, #P2645), and heparin-agarose from Sigma Chemical (St. Louis, Mo.), thrombin and antithrombin from Boehringer Mannheim (Indianapolis, Ind.), and disuccinimidyl suberate (DSS) from Pierce (Rockford, Ill.). Rapamycin was a gift of the Wyeth-Ayerst company (Philadelphia, Pa.) and FK506 a gift of the Fujisawa company (Tsukuba City, Japan).

Example 1

Rapamycin Promotes the Binding of FKBP12 to Two Cytosolic Proteins of Mr 245 and 35 kDa A $^{32}$P-radiolabeled FKBP12 probe was used to detect proteins that associate with the immunophilin in the presence of ligand, and are crosslinked to it by the bivalent reagent DSS. The probe was prepared by phosphorylating with [$\gamma$ $^{32}$P]ATP a recombinant rat FKBP12 to which two consensus sites for cyclic AMP-dependent protein kinase (PKA) were added at the N-terminus (Blanar and Rutter, 1992; Li et al., 1992). Since this modification did not alter the capacity of the protein to associate with calcineurin in the presence of FK506. the probe can be used to identify a target of the FKBP12-rapamycin complex.

PC12 pheochromocytoma cell cytosolic extracts were incubated with $^{32}$P-FKBP12 in the presence or absence of rapamycin and then treated with the crosslinker DSS before gel electrophoretic analysis followed by autoradiography. The drug caused the formation of two protein complexes with radioactive FKBP12, corresponding to bands of Mr 260 and 50 kDa (FIG. 5). Taking into account the 15 kDa Mr of the modified FKBP12 probe, the crosslinked proteins were estimated to be 245 kDa and 35 kDa, respectively. The crosslinked complexes were observed over a wide rapamycin concentration range, but were more prominent at the low concentrations of 1 and 10 nM, possibly because of an inhibitory effect on the association of the higher amounts of ethanol (the solvent of the drug) present at the higher drug concentrations (FIG. 5). Rapamycin also induced the formation of similar complexes when the probe was incubated with cytosolic extracts from several rat tissues, including liver, kidney, heart, small intestine, thymus, testes, spleen and brain, but no significant differences in abundance of the crosslinked proteins between the tissues were observed. For convenience, further experiments were carried out with whole brain extracts.

The formation of the rapamycin-dependent complexes was specific for FKBP12, since in similar experiments with the related immunophilin $^{32}$P-FKBP25, no ligand induced complexes were observed.

PC12 cells were maintained in culture as described (Altin et al., 1991). PC12 cells were lysed in homogenization buffer with 0.3% NP-40 instead of CHAPS. Lysis was accomplished in 2 ml buffer/T-150 flask by repeated vortexing at 4° C. Cell debris was sedimented by centrifugation for 10,000×g for 10 minutes at 4° C.

The labeled, cleaved FKBP12 was diluted to 10,000 cpm/ml in 50 mM Hepes pH 7.5, 1 mg/ml BSA. 10 μl of labeled protein (100,000 cpm total), 10 μl of tissue or PC12 cell extract, and 10 μl of drug dilutant buffer (20 mM Hepes 6.8, 100 mM KCl, 1 mM EGTA, 1 mM DTT) containing either 3-fold the desired final concentration of rapamycin, FK506, or equivalent amounts of ethanol, were mixed and incubated for 1 hour at 4° C. After this incubation, 1 ml of 5.5 mg/ml disuccinimidyl suberate (DSS) was added and the incubation continued for 40 minutes. The reaction was terminated by adding one column volume of 2×concentrated sample buffer (Laemmlli, 1970) containing 50 mM Tris pH 7.4 and processed by SDS-PAGE (10%, unless otherwise specified) and autoradiography.

Example 2

Specificity of the Rapamycin Induced Association: the Interaction of $^{32}$P-FKBP12-rapamycin with the 245 and 35 kDa Proteins is Competed by FK506 and by Unlabeled FKBP12

Figure 1:
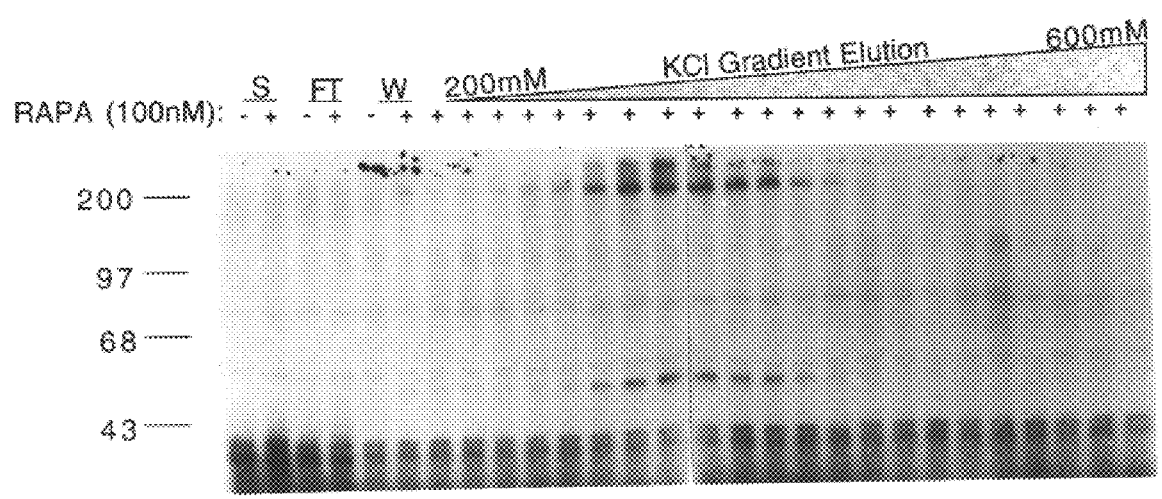
FIG. 1 shows partial purification of the FKBP12-rapamycin target proteins from brain cytosol by heparin column chromatography.

To investigate further the specificity of the interaction of $^{32}$P-FKBP12-rapamycin with the cytosolic proteins, we performed a partial purification to remove endogenous FKBP12, which is present in brain at high concentrations (Steiner et al., 1992). This was accomplished by chromatography on a heparin column, to which the cytosolic proteins that interact with FKBP12-rapamycin bound and could be eluted at 300 to 450 mM KCl (FIG. 1). Free FKBP12, on the other hand, was recovered in the flowthrough of this column, as demonstrated by binding to [$^3$H]FK506 (data not shown).

The rat brain extract was applied to a heparin column (2 ml of packed heparin-agarose per brain) at a flow, rate of 1.5 ml/min. The column was washed with 10 column volumes of buffer (20 mM Hepes pH 6.8, 200 mM KCl, 1 mM EGTA, 50 mM NaF, 1.5 mM Na$_3$VO$_4$, 4 mM DTT, 1 mM PMSF) and the same protease inhibitors as in the homogenization buffer. The material bound to the column was eluted with a linear KCl gradient from 200 to 600 mM in homogenization buffer. Aliquots (10 μl) of the fractions collected were tested in the crosslinking assay and positive fractions were pooled and concentrated in a centriprep-100 (Amicon, Beverly, Mass.) to ⅓ starting volume. The flowthrough of the heparin column was assayed for the presence of FKBP with a $^3$H-FK506 binding assay, as described (Steiner et al, 1992).

FK506 antagonizes actions of rapamycin, and both drugs compete for the same binding site on FKBP12 (Bierer et al., 1990a; Dumont et al., 1990a). Accordingly, we examined the influence of FK506 on the rapamycin-induced interaction of $^{32}$P-FKBP12 with its putative cytosolic targets. At concentrations ranging from 1 nM to 1 μM rapamycin induced the appearance of intense bands representing crosslinked proteins and, at all rapamycin concentrations tested, this effect was antagonized by 1 μM FK506 (FIG. 2A). As expected for ligands of similar affinity for FKBP12, when equal concentrations (1 μM) of rapamycin and FK506 were present, the intensities of the crosslinked bands were reduced by approximately 50% and the reduction progressively increased with increasing ratios of FK506/rapamycin. The heparin column eluate apparently contains limiting amounts of the putative targets of the FKBP12-rapamycin complex, since excess unlabeled FKBP12 (1 μM) completely suppressed the appearance of the crosslinked bands containing labeled FKBP12 (FIG. 2A).

Control experiments (FIG. 2B) confirmed the specificity of the rapamycin effect since the formation of the complex was not induced by several concentrations of FK506 or by ethanol, the solvent of the drugs. These experiments demonstrate that the crosslinked proteins are specific targets of the FKBP12-rapamycin complex and not of the FKBP12-FK506 complex, nor of FKBP12 alone. Therefore, we designate the crosslinked proteins RAFT1 (245 kDa) and RAFT2 (35 kDa) for Rapamycin And FKBP12 Target.

We attempted to separate RAFT1 and RAFT2 under nondenaturing conditions by several chromatography and gel filtration procedures. including DEAE and CM cellulose, reactive dye green 5, and Superose 6 (data not shown). All of these efforts failed, suggesting that RAFT1 and RAFT2 are part of a complex, although it is possible that RAFT2 is a proteolytic fragment of RAFT1 that contains the FKBP12-rapamycin binding site and remains tightly bound to the rest of the polypeptide.

Example 3

Purification of RAFT1

We purified RAFT1 from the heparin column eluate based on its affinity for FKBP12-rapamycin. We constructed a glutathione-S-transferase-FKBP12 fusion protein by cloning, in frame downstream of GST, a cDNA encoding FKBP12 with two N-terminal PKA consensus sites (Smith and Johnson, 1988; Blanar and Rutter, 1992; Li et al., 1992). The encoded protein was expressed in bacteria, purified and immobilized on glutathione-agarose beads. SDS-PAGE analysis of the beads recovered after incubating them with the heparin eluate in the presence or absence of rapamycin shows that the drug induces the binding to the beads of a protein of 245 kDa (FIG. 3). With this simple purification scheme we were able to purify about 5 μg of RAFT1. A low transfer efficiency to nitrocellulose membrane resulted in only 2.5 μg being available for protein sequencing, which corresponds to 10 picomoles of a protein of this size.

Standard techniques of molecular biology cloning were used as described (Sambrook et al., 1989) for the preparation of GST-(PKA)$_2$-FKBP12 and GST-(PKA)$_2$-FKBP25 fusion proteins, unless otherwise specified. All cDNAs obtained with the polymerase chain reaction were sequenced using the Sequenase kit (Amersham, Arlington Heights, Ill.). cDNAs for the rat FKBP12 and FKBP25 were obtained with the PCR using 5' and 3' primers to the corresponding human FKBP12 (Standaert et al., 1990) or FKBP25 (Jin et al., 1992) sequences. The cDNAs were cloned into pBluescript (Stratagene, La Jolla, Calif.).

A 5' primer (PKA-12-1 or PKA-25-1) encoding a BamHI site, two consensus PKA phosphorylation sites (Blanar and Rutter, 1992; Li et al., 1992), and the first 6 amino acids of FKBP12 or FKBP25 was used with a 3' primer (PKA-12-2 or PKA-25-2) encoding an EcoRI site and the last 6 codons of FKBP12 or FKBP25 in a PCR with Vent Polymerase (New England Biolabs, Beverly, Mass.) using the rat FKBPs cDNAs cloned in pBluescript as templates. The amplified DNA fragments were gel purified, digested with BamnH1 and EcoR1 and cloned into the pGEX-2T vector (Pharmacia, Upsala, Sweden) that had been linearized with the same restriction enzymes. The resulting construct was used to transform BL21 (DE3) *E. coli* (Novagen, Madison, Wis.) in which expression can be induced with IPTG. The primer sequences were is follows:

PKA-12-1:5' CCGGATCCCGTCGAGCTTCAGT-TGAACTACGGCGTGC TTCTGTAGCCATGG-GAGTGCAGGTGGA 3' (SEQ ID NO:4)

PKA-12-2: 5' GGCCGGAATTCTCATTCCAGTTTTA-GAA 3' (SEQ ID NO:5)

PKA-25-1: 5' CCGGATCCCGTCGAGCTTCAGT-TGAACTACGGCGTGC TTCTGTAGCCATGGCG-GCGGCCGTTCC 3' (SEQ ID NO:10)

PKA-25-2: 5' GGCCGGAATTCTCAATCAATATC-CACTA 3' (SEQ ID NO:11)

The fusion proteins were purified with glutathione-agarose as previously described (Smith and Johnson, 1988) from bacterial cultures induced with 1 mM IPTG.

The concentrated heparin column eluate was incubated for 2 hours at 4° C. with 1/50 volume of glutathione-agarose to remove endogenous glutathione binding proteins. The beads were removed by centrifugation at 1000×g for 3 minutes. Fresh glutathione-agarose (1/500 volume) and 20 μg of purified GST-PKA-FKBP12 fusion protein were then added to the cleared heparin column eluate with or without 100 nM rapamycin. After a 1 hour incubation at 4° C., the bead were washed 5× with 1.5 ml ice-cold PBS containing 1% Triton X-100 and 500 mM NaCl. The beads were transferred to 3×volume SDS-PAGE sample buffer, and the eluted proteins fractionated by SDS-PAGE and the gel silver stained.

Whether RAFT2 was also bound to the beads could not be determined in this experiment, because its presence would be masked by the large band of similar Mr corresponding to the GST-(PKA)$_2$-FKBP12 fusion protein. When smaller fusion proteins, such as an epitope-tagged FKBP12, were employed for the affinity matrix, the binding of the 35 kDa RAFT2 could also be observed.

The immunophilin fusion proteins containing N-terminal phosphorylation sites for PKA were labeled with a modification of published procedures (Blanar et. al., 1992, Li et. al., 1992). 10 ng of purified GST-PKA-FKBP12 or 25 was mixed with 40 units of PKA and 100 mCi of [γ-P$^{32}$]-ATP in a buffer containing 20 mM Hepes pH 7.7, 100 mM NaCl, 12 mM MgCl$_2$, 1 mM DTT.

After a 1.5 hour at 37° C. the incubation mixture containing labeled fusion protein was dialyzed twice against 1 L of thrombin cleavage buffer (50 mM Tris pH 7.4, 150 mM NaCl, 2.5 mM CaCl$_2$). The labeled fusion protein was cleaved by adding an equal volume of thrombin cleavage buffer containing 2 mg/ml thrombin and incubating at room temperature for 2 hours. The thrombin was inactivated by adding an equal volume of a stop solution consisting of 1 mM DTT, 1 mM PMSF, 100 units/ml antithrombin III. The specific activity of the probes was estimated at 1×10$^5$ cpm/pmol of the protein.

Example 4

Protein Sequencing of RAFT1: Homology to TOR1 and TOR2

Affinity purified RAFT1 was separated by SDS-polyacrylamide gel electrophoresis from other proteins that adsorbed to the glutathione-agarose beads, transferred to nitrocellulose membrane, and digested with trypsin. Fractionation of the tryptic digest by narrow-bore reverse phase chromatography yielded a complex pattern of over a hundred peaks whose purity was assessed by mass spectroscopy. In most cases, the peaks exhibited multiple mass to charge peak values and it was necessary to rechromatograph these peak fractions on a microbore columns of different selectivity.

For protein sequence analysis affinity purified material derived from 50 brains was fractionated by SDS-PAGE and transferred to nitrocellulose membranes. The proteins transferred were visualized by Ponceau S staining, the 245 kDa RAFT1 band excised and processed for internal amino acid sequence analysis, essentially as described (Tempst et al., 1990).

Membrane-bound protein, about 2.5 μg, was subjected to in-situ proteolytic cleavage using 1 μg trypsin (Sequencing Grade; Boehringer-Mannheim) in 25 ml 100 mM NH$_4$HCO$_3$ (supplemented with 10% acetonitrile and 3% Tween-80) at 37° C. for 3 hours. The resulting peptide mixture was reduced and S-alkylated with, respectively, 0.1% β-mercapto ethanol and 0.3% 4-vinyl pyridine, and fractionated by two-dimensional reversed phase HPLC.

For the primary separations, a 2.1 mm Vydac C4 (214TP54) column was used with gradient elution at a flow rate of 100 μl/min. HPLC solvents and system configuration were as described (Tempst et al., 1990), with improved dead volume reduction through the use of glass capillary tubing (Elicone and Tempst, unpublished). Identification of Trp-containing peptides was done by manual ratio analysis of absorbances at 297 and 277 nm, monitored in real time using an Applied Biosystems model 1000S diode-array detector (Tempst et al., 1990). Fractions were collected by hand, kept on ice for the duration of the run and then stored at –70° C. before repurification and/or analysis. An enzyme blank was done on an equally sized strip of nitrocellulose cut from a blank area of the same blot. Repurifications (second dimension LC) were carried out on a 1.0 mm SGE ODS-2 C18 column using the same solvent system but at a flow rate of 30 μl/min. (C. Elicone, M. Lui, S. Geromanos, H. Erdjument-Bromage, P. Tempst, in press). Samples were always acidified (20% TFA final concentration) and then diluted twofold with 0.1% TFA before rechromatography.

Sequences of 23 peptides separated in this fashion were determined by a combination of automatic Edman degradation, matrix-assisted laser desorption mass-spectroscopy, and UV spectroscopy.

Peak fractions over background were analyzed by a combination of automated Edman degradation and matrix-assisted laser-desorption (MALDI-TOF) mass spectrometry (Geromanos et al., 1994; Elicone et al., 1994). After storage, column fractions were supplemented with neat TFA (to give a final concentration of 10%) before loading onto the sequencer disc and mass spectrometer probe tips. Peptide mass analysis (on 2% aliquots) was carried out using a model LaserTec ReseaRcH MALDI-TOF instrument (Vestec), with a 337 nm output nitrogen laser and 1.2 m flight tube. The matrix was a-cyano-4-hydroxy cinnamic acid, and a 28 kV ion acceleration and 4.3 kV multiplier voltage were used. Laser power and number of acquisitions were adjusted as judged from optimal deflections of specific maxima, using a Tektronix TDS 520 digitizing oscilloscope. M/z (mass to charge) spectra were generated from the time-of-flight files using GRAMS data analysis software. Every sample was analyzed twice, in the presence and absence of a calibrant (25 femtomoles APID), as described (Geromanos et al., 1994). Chemical sequencing (on 95% of the sample) was clone using a model 477A instrument from Applied Biosystems (AB). Stepwise liberated PTH-amino acids were identified using an "on-line" 120A HPLC system (AB) equipped with a PTH C18 (2.1×220 mm; 5 micron particle size) column (AB). Instruments and procedures were optimized for femtomole level phenyl thiohydantoin amino acid analysis as described (Tempst and Riviere, 1990; Erdjument-Bromage et al., 1993).

Peptide average isotopic masses were summed from the identified residues (including the presumed ones) using ProComp version 1.2 software (obtained from Dr. P. C. Andrews, University of Michigan, Ann Arbor, Mich.). Peptide sequences were compared to entries in various sequence databases using the National Center for Biotechnology Information (NCBI) BLAST program (Altschul et al. 1990). Lower stringency alignments between all peptides and selected proteins were done using the Lipman-Pearson algorithm, available in the 'Lasergene' software package (DNASTAR).

Several protein sequence databases (PIR, SwissProt, translated Genbank) were searched for sequences that match any of the 23 peptide sequences obtained from microsequencing of RAFT1. While sequence similarities with hundreds of different proteins were obtained for many of the 23 peptides, none perfectly matched with any of the entries in the databases, nor did any protein match more than one or two peptides, other than the yeast proteins TOR1 and TOR2 (Kunz et al., 1993). Strikingly, sixteen out of the 23 peptides of RAFT1 could be aligned with the yeast TOR sequences, with varying degrees of similarity (FIG. 4).

Example 5

Molecular Cloning of RAFT1

To generate a probe for isolating a RAFT1 cDNA two degenerate oligonucleotides were used in a mixed oligonucleotide polymerase chain reaction (PCR) (Gould et al, 1989) with rat brain cDNA as template. The sense primer was made to a peptide sequence (TYDPNQP, SEQ ID NO:6) obtained from microsequencing of RAFT1, while the antisense primer corresponds to a sequence (HIDFGD, SEQ ID NO:7) conserved between TOR1, TOR2, and p110 PI-3 Kinase. From the alignments of the RAFT1 peptides to the TORs, this sequence was expected to be 220 amino acids downstream of that encoded by the sense primer. The predicted 660 bp PCR product was obtained, cloned, and its authenticity was verified by DNA sequencing, which showed that it encoded two other sequenced tryptic peptides. The PCR product was, therefore, used as a probe (3' probe) to screen a rat striatum cDNA library, which yielded a 5.5 kb partial cDNA clone. An antisense oligonucleotide to the extreme 5' end of this cDNA was then used in a PCR reaction with a degenerate sense oligonucleotide to another peptide sequence (NDQVFE, SEQ ID NO:8) obtained from microsequencing. The predicted 1.1 kb PCR product was obtained, cloned and used as probe (5' probe) to screen a rat brainstem cDNA library in parallel with the original 3' probe. Phage plaques that hybridized with both probes were isolated and one was found to carry a 8.6 kb insert. A degenerate sense oligpnucleotide corresponding to the amino acid sequence TYDPNQP (SEQ ID NO:6), which was obtained from microsequencing of RAFT1 and aligns to residues 2086 to 2093 of TOR2, and a degenerate antisense primer corresponding to amino acids 2296 to 2301 (HIDFGD, SEQ ID NO:7) of TOR2 were used in a PCR reaction with rat whole brain cDNA as template. The protocol for the PCR was: an initial 5 min at 94° C., followed by 35 cycles of 94° C. for 40s, 56° C. for 1 min, 72° C. for 1 min, and a final incubation at 72° C. for 5 min. The PCR products were fractionated on a 1.1% agarose gel, the expected 700 bp DNA fragment purified and subcloned into pBluescript.

The RAFT-1 cDNA fragment in pBluescript was amplified by PCR, the product gel purified and labeled by nick translation with a commercial kit (Boehringer Mannheim). This probe (designated 3' probe) was used to screen $1\times10^6$ phage plaques of a rat striatum λ ZAP library (Stratagene), as described (Sambrook et al.). Forty seven positive clones were identified and 10 of them were purified by an additional two rounds of screening. None of the inserts contained a complete open reading frame. The 5' end of the largest insert (5.5 kb) was used to design a 18 bp antisense oligdnucleotide (3.1 as) that was used in another PCR reaction with rat whole brain cDNA as template and a degenerate oligonucleotide corresponding to the amino acid sequence NDQVFE (SEQ ID NO:8, part of a peptide obtained from microsequencing) as the sense primer. The PCR products were fractionated on a 1% agarose gel and a DNA fragment of 1.1 kb isolated and cloned into the vector pCR-II using the TA cloning kit (Invitrogen, San Diego, Calif.). The cDNA fragment was amplified by PCR, the product gel purified and labeled by nick translation. This probe (designated 5' probe) was used to screen $1\times10^6$ phage plaques from a rat brainstem λ ZAP library. Duplicate filters were screened with the 3' probe. Eight clones hybridized with both the 5' and 3' probes, and five of these were purified through 2 additional rounds of screening. One clone contained a 8.6 kb insert that encodes all 23 peptide sequences obtained by microsequencing.

PCR primer sequences were as follows:

TYDPNQP (SEQ ID NO:6): 5'-GGGGGATCCACNTA(C/T)GA(C/T)CCNAA(C/T) CA(A/G)C-3' (SEQ ID NO:12)

HIDFGD (SEQ ID NO:7): 5'-GCGGAATTC(G/A)TCNCC(G/A)AA(G/A)TC(T/G/A) AT(G/A)TG-3' (SEQ ID NO:13)

NDQVFE (SEQ ID NO:8): 5'-GGGGGATCCAA(C/T)GA(C/T)CA(G/A)GTNTT (T/C)GA-3' (SEQ ID NO:14)

3.1as: 5'-GAGCCACCACGATTTGCT-3'(SEQ ID NO:9)

cDNA clones were sequenced using the flourescent terminator method of cycle sequencing on a Applied Biosystems 373a automated DNA sequencer at the DNA analysis Facility of the Johns Hopkins University (Smith et al., 1986; McCombie et al, 1992), or with the dideoxy chain termination method using the Sequenase kit (Amersham, Arlington Heights, Ill.). Oligonucleotides used for sequencing were synthesized on an ABI 394 synthesizer following ABI protocols. DNA sequence data was analyzed using Sequencher software from Gene Codes (Ann Arbor, Mich.). Protein alignments were done with help from the e-mail service of the Computational Biochemistry Research Group (CBRG) at the ETH.

This cDNA contains an open reading frame of 7.6 kb with an initiation methionine codon that conforms to the Kozak consensus sequence (Kozak, 1986) and is preceded by an in-frame termination codon. The protein encoded by this open reading frame contains all 23 peptide sequences obtained by microsequencing of RAFT1 (FIG. 4). Interestingly, none of the peptides sequenced correspond to the C-terminal 250 amino acids of RAFT1, which may indicate that this portion of the protein was proteolytically removed during the purification.

The RAFT1 cDNA predicts a protein of 2550 amino acids with a molecular mass of 289 kDa and a PI of 6.8. Over its entire sequence RAFT1 is 43% identical to TOR2 and 39% identical to TOR1 (FIG. 4). The C-terminal 600 amino acids of RAFT1, which, by analogy to the TORs (Cafferkey et al., 1993; Kunz et al., 1993; Helliwell et al., 1994), is predicted to contain lipid kinase activities, is 65% identical to the yeast proteins. The RAFT1 protein has over 20 consensus sites for phosphorylation by protein kinase C (PKC), including one at serine$_{2035}$, which is in the analogous position to the serine ($S_{1972}$ in TOR1 and $S_{1975}$ in TOR2) found mutated to arginine in rapamycin resistant yeast (boxed residues in FIG. 4).

The predicted RAFT1 protein is 80 amino acids longer than the TOR proteins, and contains several regions with no apparent homology to the yeast proteins, the largest being a 93 amino acid insertion corresponding to residues 270 to 363 of RAFT1. It is possible that these regions are generated by alternative splicing of exons that may be tissue specific to the brain. They are unlikely to be the translation product of unspliced introns because they were found in several cDNA clones isolated from different libraries and the DNA sequence does not reveal consensus splice junction sites.

REFERENCES

The following references are incorporated herein by reference:

Albers, M. W., Williams, R. T., Brown, E. J., Tanaka, A., Hall, F. L., and Schreiber, S. L. (1993). FKBP-Rapamycin inhibits a cyclin-dependent kinase activity and a cyclin D1-Cdk association in early G1 of an osteosarcoma cell line. J. Biol. Chem. 268, 22825–22829.

Altin, J. G., Kujubu, D. A., Raffioni, S., Ereleth, D. D., Herschman, H. R. and Bradshaw, R. A. (1991). Differential induction of primary-response (TIS) genes in PC12 pheochromocytoma cells and the unresponsive variant PC12nnr5. J. Biol. Chem. 266, 5401–5406.

Altschul, S. F., Gish, W., Miller, W., Myers, E. W., and Lipman, D. J. (1990). Basic local alignment search tool. J. Mol. Biol. 215, 403–410.

Auger, K. R., Serunian, L. A., Soltoff, S. P., Libby, P., and Cantley, L. C. (1989). PDGF-dependent tyrosine phosphorylation stimulates production of novel polyphosphoinositides in intact cells. Cell 57, 167–175.

Balla, T., Sim, S. S., Baukal, A. J., Rhee, S. G., Catt, K. J. (1994). Inositol polyphosphates are not increased by overexpression of Ins(1,4,5)P3 3-kinase but show cell-cycle dependent changes in growth factor-stimulated fibroblasts. Molec. Biol. of the Cell 5, 17–27.

Bierer, B. E., Mattila, P. S., Standaert, R. F., Herzenberg, L. A., Burakoff, S. J., Crabtree, G., and Schreiber, S. L. (1990a). Two distinct signal transduction pathways in T lymphocytes are inhibited by the complexes formed between an immunophilin and either FK506 or rapamycin. Proc. Natl. Acad. Sci. USA 87, 9231–9235.

Bierer, B. E., Somers, P. K., Wandless, T. J., Burakoff, S. J., and Schreiber, S. L. (1990b). Probing immunosuppressant action with a nonnatural immunophilin ligand. Nature 250, 556–559.

Blanar, M. A. and Rutter, W. J. (1992). Interaction cloning: identification of a helix-loop-helix zipper protein that interacts with c-Fos. Nature 256, 1014–1018.

Borel, J. F. (1986). Ciclosporin. Progr. Allergy 38, 9–18.

Cafferkey, R., Young, P. R., McLaughlin, M. M., Bergsma, D. J., Koltin, Y., Sathe, G. M., Faucette, L., Eng, W., Johnson, R. K., and Livi, G. P. (1993). Dominant missense mutations in a novel yeast protein related to mammalian phosphatidylinositol 3-kinase and VPS34 abrogate rapamycin cytotoxicity. Molec. and Cell. Biol. 13, 6012–6023.

Cantley, L. C., Auger, K. R., Carpenter, C., Ducksworth, B., Graziani, A., Kapeller, R., and Solotoff, S. (1991). Oncogenes and signal transduction. Cell 64, 281–302.

Carpenter, C. L., Ducksworth, B. C., Suger, K. R., Cohen, B., Chaffilausen, B. S., and Cantley, L. C. (1990). Purification and characterization of phosphoinositide 3-kinase from rat liver. J. Biol. Chem. 265, 19704–19711.

Chung, C., Kuo, C. J., Crabtree, G. R., and Blenis, J. (1992). Rapamycin-FKBP specifically blocks growth-dependent activation and signaling by the 70 kD S6 protein kinases. Cell 69, 1227–1236.

Dumont, F. J., Melino, M. R., Staruch, M. J., Koprak, S. L., Fischer, P. A., and Sigal, N. H. (1990a). The immunosuppressive macrolides FK506 and rapamycin act as reciprocal antagonists in murine T cells. J. Immunol. 144, 251–258.

Dumont, F. J., Staruch, M. J., Koprak, S. L., Melino, M. R., and Sigal, N. H. (1990b). Distinct mechanisms of suppression of murine T-cell activation by the related macrolides FK-506 and rapamycin. J. Immunol. 144, 251–258.

Erdjument-Bromage, H., Geromanos, S., Chodera, A., and Tempst, P. (1993). Successful peptide sequencing with femtomole level PTH-analysis: a commentary. In Techniques in Protein Chemistry, Vol. 4, R. H. Angeletti, ed. (San Diego, Calif.: Academic Press) pp. 419–426.

Flanagan, W. M., Corthesy, B., Bram, R. J., and Crabtree, G. R. (1991). Nuclear association of a T-cell transcription factor blocked by FK506 and cyclosporin A. Nature 352, 803–807.

Fruman, D. A., Burakoff, S. J., and Bierer, B. E. (1994). Immunophilins in protein folding and immunsuppression. FASEB J. 8, 391–400.

Geromanos, S., Casteels, P., Elicone, C., Powell, M., and Tempst, P. (1994). Combined Edman-chemical and laser-desorption mass spectrometric approaches to micro peptide sequencing: optimization and applications. In Techniques in Protein Chemistry, Vol. 5, J. W. Crabb, ed. (San Diego, Calif.: Academic Press) pp. 143–150.

Gould, S. J., Subramani, S., and Scheffler, I. E. (1989). Use of the DNA polymerase chain reaction for homology probing: isolation of partial cDNA or genomic clones encoding the iron-sulfur protein of succinate dehydrogenase from several species. Proc. Natl. Acad. Sci. USA 86, 1934–1938.

Handschumacher, R. E., Harding, M. W., Rice, J., Drugge, R. J. and Speicher, D. W. (1984). Cyclophilin: a specific cytosolic binding protein for cyclosporin A. Nature 226, 544–546.

Harding, M. W., Galat, A., Uehling, D. E., and Schreiber, S. L. (1989). A receptor for the immunosuppressant FK506 is a cis-trans peptidyl-prolyl isomerase. Nature 341, 758–760.

Heitman, J. Movva, N. R. and Hall, M. N. (1991a). Targets for cell cycle arrest by the immunosuppressive agent rapamycin in yeast. Nature 253, 905–909.

Heitman, J. Movva, N. R., Hiestand, P. C., and Hall, M. N. (1991b). FK506-binding protein proline rotamase is a target for the immunosuppressant rapamycin in yeast. Proc. Natl. Acad. Sci. USA 88, 1948–1952.

Heitman, J., Movva, N. R., and Hall, M. N. (1992). Proline isomerases at the crossroads of protein folding, signal transduction, and immunosuppression. New Biologist 4, 448–460.

Helliwell, S. B., Wagner, P. Kunz, J., Deuter-Reinhard, M., Henriquez, R., and Hall, M. N. (1994). TOR1 and TOR2 are structurally and functionally similar but not identical phosphatidylinositol kinase homologues in yeast. Mol. Biol. Cell 5, 105–118.

Jayararnan, T., Brillantes A. M., Timerman, A. P., Fleischer, S., Erdjument-Bromage, H., Tempst, P., and Marks, A. R. (1992). FK506 binding protein associated with the calcium release channel (ryanodine receptor). J. Biol. Chem. 267, 9474–9477.

Jayaraman, T. and Marks, A. R. (1993). Rapamycin-FKBP12 blocks proliferation, induces differentiation and inhibits cdc2 kinase activity in a myogenic cell line. J. Biol. Chem. 268, 25385–25388.

Jin Y. J., Burakoff, S. J., and Bierer B. E. (1992). Molecular cloning of a 25-KDa high affinity rapamycin binding protein, FKBP25. J. Biol. Chem. 267, 10942–10945.

Kino, T., Hatanaka, H., Miyata, S., Inamura, N., Nishiyama, M., Yajima, T., Gotto, T., Okuhara, M., Aoki, H., and Ochiai, T. (1987). FK-506, a novel immunosuppressive agent isolated from a Streptomycetes. II. Immunosuppressive effect of FK-506 in vitro. J. Antibiotics 60, 1249–1265.

Kozak, M. (1986). An analysis of 5'-noncoding sequences from 699 vertebrate messenger RNAs. Nucl. Acids Res. 15, 8125–8132.

Kronke, M., Leonard, W., Depper, J., Ayra, S., Wong-Staal, F., and Gallo, R. (1984). Cyclosporin A inhibits T-cell growth factor gene expression at the level of mRNA transcription. Proc. Natl. Sci. Acad. USA 81, 5214–5218.

Kunz, J. and Hall, M. N. (1993). Cyclosporin A, FK506, and rapamycin: more than just immunosuppression. Trends Biochem. Sci. 18, 334–338.

Kunz, J., Henriquez, R., Schneider, U., Deuter-Reinhard, M., Movva, N. R., and Hall, M. N. (1993). Target of rapamycin in yeast, TOR2, is an essential phosphatidyl kinase homolog required for $G_1$ progression. Cell 73, 585–596.

Kuo, C. J., Chung, J., Fiorentino, D. F., Flanagan, W. M., Blenis, J., and Crabtree, G. R. (1992). Rapamycin selectively inhibits interleukin-2 activation of p70 S6 kinase. Nature 358, 70–73.

Laemmli, U. K. (1970). Cleavage of structural proteins during assembly of the head of the bacteriophage T4. Nature 227, 680–685.

Li, M., Jan, Y. N., and Jan, L. Y. (1992). Specific interaction of subunit assembly by the hydrophillic amino-terminal domain of the shaker potassium channel. Science 257, 1225–1230.

Li, W. and Handschumacher, R. E. (1993). Specific interaction of the cyclophilin-cyclosporin complex with the B subunit of calcineurin. J. Biol. Chem. 268, 14040–14044.

Liu, J. (1993). FK506 and ciclosporin: molecular probes for studying intracellular signal transduction. Trends Pharm. Sci. 14, 182–188.

Liu, J., Farmer, J. D., Jr., Lane, W. S., Friedman, I., and Schreiber, S. L. (1991). Calcineurin is a common target of the cyclophilin-cyclosporin A and FKBP-FK506 complexes. Cell 66, 807–815.

Martel, R. R., Klicius, J., and Galet, S. (1977). Inhibition of the immune response by rapamycin, a new antifungal antibiotic. Can. J. Physiol. Pharm. 55, 48–51.

McCombie, W. R., Heiner, C., Kelly, J. M., Fitzgerald, M. G., Gocayne, J. D. (1992). Rapid and reliable flourescent cycle sequencing of double stranded templates. DNA Sequence 2, 289–296.

Morice, W. G., Wiederrecht, G., Brunn, G. J., Siekierka, J. J., and Abraham, R. T. (1993). Rapamycin inhibition of interleukin-2-dependent p33cdk2 and p34cdc2 kinase activation in T lymphocytes. J. Biol. Chem. 268, 22737–22745.

Sambrook, J., Fritsch, E. F., and Maniatis, T. (1989). Molecular Cloning: A Laboratory Manual, Second Edition (Cold Spring Harbor, N.Y.: Cold Spring Harbor Laboratory Press).

Schreiber, S. L. (1991). Chemistry and biology of the immunophilins and their immunosuppressive ligands. Nature 251, 283–287.

Siekierka, J. J., Hung, S. H. Y., Poe, M., Lin, C. S., and Sigal, N. H. (1989). A cytosolic binding protein for the immunosuppressant FK506 has peptidyl-prolyl isomerase activity but is distinct from cyclophilin. Nature 341, 755–757.

Smith, D. B., and Johnson, K. S. (1988). Single-step purification of polypeptides expressed in *Escherichia coli* as fusions with glutathione S-transferase. Gene 67, 31–40.

Smith, L. M., Sander, J. Z., Kaiser R. J., Hughes, P., Dodd, C., Connel, C. R., Heiner, C., Kent, S. B., Hood L. E. (1986) Flouresence detection in automated sequence analysis. Nature 321, 674–679.

Standaert, R. F., Galat, A., Verdine, G. L., and Schreiber, S. L. (1990). Molecular cloning and overexpression of the human FK506-binding protein, FKBP. Nature 346, 671–674.

Steiner, J. P., Dawson, T. M., Fotuhi, M., Glatt, C. E., Snowman, A. M., Cohen, N., and Snyder, S. H. (1992). High brain densities of the immunophilin FKBP colocalize with calcineurin. Nature 358, 584–587.

Tempst, P., Link, A. J., Riviere, L. R., Fleming, M., and Elicone, C. (1990). Internal sequence analysis of proteins separated on polyacrylamide gels at the sub-microgram level: improved methods, applications and gene cloning strategies. Electrophoresis 11, 537–553.

Tempst, P., and Riviere, L. (1989). Examination of automated polypeptide sequencing using standard phenyl isothiocyanate reagent and subpicomole high performance liquid chromatographic analysis. Anal. Biochem. 183, 290–300.

Timerman, A. P., Ogunbummi, E., Freund, E., Wiederrecht, G., Marks, A. R., and Fleischer, S. (1993). The calcium release channel of sarcomplasmic reticulum is modulated by FK506-binding-protein. J. Biol. Chem. 268, 22992–22999.

Tropschug, M., Barthelmess, I. B., and Neupert, W. (1989). Sensitivity to cyclosporin A is mediated by cyclophilin in Neurospora crassa and Saccharomyces cerevisiae. Nature 342, 953–957.

Whitman, M., Downes, C. P., Keeler, M., Keller, T., and Cantley, L. (1988). Type I phosphotidylinositol kinase makes a novel inositol phospholipid, phosphatidylinositol-3-phosphate. Nature 332, 644–646.

What is claimed is:

1. A rat RAFT1 protein prepared by the process of:
   (a) contacting a preparation of rat proteins with FKBP12 in the presence of 1 to 10 nM rapamycin;
   (b) isolating rat proteins which bind to FKBP12 in the presence of 1 to 10 nM rapamycin from those rat proteins which do not bind in the presence of 1 to 10 nM rapamycin;
   (c) dissociating bound rat proteins from FKBP12 to provide a rat RAFT1 protein.

2. An isolated and purified RAFT1 protein having the amino acid sequence as shown in SEQ ID NO:1, wherein the acronym RAFT connotes a rapamycin and FKBP12 target.

* * * * *

UNITED STATES PATENT AND TRADEMARK OFFICE
CERTIFICATE OF CORRECTION

PATENT NO.    : 6,476,200 B1                                          Page 1 of 1
DATED         : November 5, 2002
INVENTOR(S)   : David M. Sabatini et al.

It is certified that error appears in the above-identified patent and that said Letters Patent is hereby corrected as shown below:

<u>Title page, Item [54] and Column 1, lines 1-3,</u>
Title, "MAMMALIAN PROTEINS THAT BIND TO FKBP12 IN A RAMAMYCIN-DEPENDANT FASHION" has been replaced with -- RAT PROTEINS THAT EXHIBIT RAPAMYCIN-DEPENDANT BINDING TO FKBP12 --, <u>Title page,</u>
Item [73], Assignee, -- Sloan-Kettering Institute for Cancer Research, New York, NY -- has been added.

Signed and Sealed this

Eighth Day of July, 2003

JAMES E. ROGAN
*Director of the United States Patent and Trademark Office*

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 2549 amino acids
        (B) TYPE: amino acid
        (D) TOPOLOGY: linear (ii) MOLECULE TYPE: protein (iii) HYPOTHETICAL: YES (iv) ANTI-SENSE: NO (vi) ORIGINAL SOURCE:
        (A) ORGANISM: Rattus rattus
        (F) TISSUE TYPE: pheochromocytoma
        (G) CELL TYPE: PC12

(xi) SEQUENCE DESCRIPTION: SEQ ID NO:1:

```
Met Leu Gly Thr Gly Pro Ala Thr Ala Thr Ala Gly Ala Ala Thr Ser
1               5                   10                  15

Ser Asn Val Ser Val Leu Gln Gln Phe Ala Ser Gly Leu Lys Ser Arg
            20                  25                  30

Asn Glu Glu Thr Arg Ala Lys Ala Ala Lys Glu Leu Gln His Tyr Val
        35                  40                  45

Thr Met Glu Leu Arg Glu Met Ser Gln Glu Glu Ser Thr Arg Phe Tyr
    50                  55                  60

Asp Gln Leu Asn His His Ile Phe Glu Leu Val Ser Ser Ser Asp Ala
65                  70                  75                  80

Asn Glu Arg Lys Gly Gly Ile Leu Ala Ile Ala Ser Leu Ile Gly Val
                85                  90                  95

Glu Gly Gly Asn Ser Thr Arg Ile Gly Arg Phe Ala Asn Tyr Leu Arg
            100                 105                 110

Asn Leu Leu Pro Ser Ser Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270
```

-continued

```
Arg Ile Ser Ser Met Glu Gly Glu Arg Leu Arg Glu Glu Met Glu Glu
            275                 280                 285

Ile Thr Gln Gln Gln Leu Val His Asp Lys Tyr Cys Lys Asp Leu Met
        290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
                325                 330                 335

Ser Ser His Gln Gly Leu Met Gly Phe Gly Ala Ser Pro Ser Pro Thr
            340                 345                 350

Lys Ser Thr Leu Val Glu Ser Arg Cys Cys Arg Asp Leu Met Glu Glu
            355                 360                 365

Lys Phe Asp Gln Val Cys Gln Trp Val Leu Lys Cys Arg Ser Ser Lys
        370                 375                 380

Asn Ser Leu Ile Gln Met Thr Ile Leu Asn Leu Leu Pro Arg Leu Val
385                 390                 395                 400

Ala Phe Arg Pro Ser Ala Phe Thr Asp Thr Gln Tyr Leu Gln Asp Thr
                405                 410                 415

Met Asn His Val Leu Ser Cys Val Lys Lys Glu Lys Glu Arg Thr Ala
            420                 425                 430

Ala Phe Gln Ala Leu Gly Leu Leu Ser Val Ala Val Arg Ser Glu Phe
        435                 440                 445

Lys Val Tyr Leu Pro Arg Val Leu Asp Ile Ile Arg Ala Ala Leu Pro
450                 455                 460

Pro Lys Asp Phe Ala His Lys Arg Gln Lys Thr Val Gln Val Asp Ala
465                 470                 475                 480

Thr Val Phe Thr Cys Ile Ser Met Leu Ala Arg Ala Met Gly Pro Gly
                485                 490                 495

Ile Gln Gln Asp Ile Lys Glu Leu Leu Glu Pro Met Leu Ala Val Gly
            500                 505                 510

Leu Ser Pro Ala Leu Thr Ala Val Leu Tyr Asp Leu Ser Arg Gln Ile
        515                 520                 525

Pro Gln Leu Lys Lys Asp Ile Gln Asp Gly Leu Leu Lys Met Leu Ser
530                 535                 540

Leu Val Leu Met His Lys Pro Leu Arg His Pro Gly Met Pro Lys Gly
545                 550                 555                 560

Leu Ala His Gln Leu Ala Ser Pro Gly Leu Thr Thr Leu Pro Glu Ala
                565                 570                 575

Ser Asp Val Ala Ser Ile Thr Leu Ala Leu Arg Thr Leu Gly Ser Phe
            580                 585                 590

Glu Phe Glu Gly His Ser Leu Thr Gln Phe Val Arg His Cys Ala Asp
        595                 600                 605

His Phe Leu Asn Ser Glu His Lys Glu Ile Arg Met Glu Ala Ala Arg
610                 615                 620

Thr Cys Ser Arg Leu Leu Thr Pro Ser Ile His Leu Ile Ser Gly His
625                 630                 635                 640

Ala His Val Val Ser Gln Thr Ala Val Gln Val Val Ala Asp Val Leu
                645                 650                 655

Ser Lys Leu Leu Val Val Gly Ile Thr Asp Pro Asp Pro Asp Ile Arg
            660                 665                 670

Tyr Cys Val Leu Ala Ser Leu Asp Glu Arg Phe Asp Ala His Leu Ala
        675                 680                 685

Gln Ala Glu Asn Leu Gln Ala Leu Phe Val Ala Leu Asn Asp Gln Val
```

-continued

```
        690                 695                 700
Phe Glu Ile Arg Glu Leu Ala Ile Cys Thr Val Gly Arg Leu Ser Ser
705                 710                 715                 720

Met Asn Pro Ala Phe Val Met Pro Phe Leu Arg Lys Met Leu Ile Gln
                725                 730                 735

Ile Leu Thr Glu Leu Glu His Ser Gly Ile Gly Arg Ile Lys Glu Gln
                740                 745                 750

Ser Ala Arg Met Leu Gly His Leu Val Ser Asn Ala Pro Arg Leu Ile
                755                 760                 765

Arg Pro Tyr Met Glu Pro Ile Leu Lys Ala Leu Ile Leu Lys Leu Lys
                770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Val Ile Ile Met Asp Met Leu Gln Asp Ser Ser
                820                 825                 830

Leu Leu Ala Lys Arg Gln Val Ala Leu Trp Thr Leu Gly Gln Leu Val
                835                 840                 845

Ala Ser Thr Gly Tyr Val Val Glu Pro Tyr Arg Lys Tyr Pro Thr Leu
                850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
                900                 905                 910

Ser Ala Val Ser Leu Ser Glu Ser Lys Ser Ser Gln Asp Ser Ser Asp
                915                 920                 925

Tyr Ser Thr Ser Glu Met Leu Val Asn Met Gly Asn Leu Pro Leu Asp
                930                 935                 940

Glu Phe Tyr Pro Ala Val Ser Met Val Ala Leu Met Arg Ile Phe Arg
945                 950                 955                 960

Asp Gln Ser Leu Ser His His Thr Met Val Val Gln Ala Ile Thr
                965                 970                 975

Phe Ile Phe Lys Ser Leu Gly Leu Lys Cys Val Gln Phe Leu Pro Gln
                980                 985                 990

Val Met Pro Thr Phe Leu Asn Val Ile Arg Val Cys Asp Gly Ala Ile
                995                 1000                1005

Arg Glu Phe Leu Phe Gln Gln Leu Gly Met Leu Val Ser Phe Val Lys
                1010                1015                1020

Ser His Ile Arg Pro Tyr Met Asp Glu Ile Val Thr Leu Met Arg Glu
1025                1030                1035                1040

Phe Trp Val Met Asn Thr Ser Ile Gln Ser Thr Ile Ile Leu Leu Ile
                1045                1050                1055

Glu Gln Ile Val Val Ala Leu Gly Gly Glu Phe Lys Leu Tyr Leu Pro
                1060                1065                1070

Gln Leu Ile Pro His Met Leu Arg Val Phe Met His Asp Asn Ser Gln
                1075                1080                1085

Gly Arg Ile Val Ser Ile Lys Leu Leu Ala Ala Ile Gln Leu Phe Gly
                1090                1095                1100

Ala Asn Leu Asp Asp Tyr Leu His Leu Leu Pro Pro Ile Val Lys
1105                1110                1115                1120
```

-continued

```
Leu Phe Asp Ala Pro Glu Val Pro Leu Pro Ser Arg Lys Ala Ala Leu
            1125                1130                1135
Glu Thr Val Asp Arg Leu Thr Glu Ser Leu Asp Phe Thr Asp Tyr Ala
            1140                1145                1150
Ser Arg Ile Ile His Pro Ile Val Arg Thr Leu Asp Gln Ser Pro Glu
            1155                1160                1165
Leu Arg Ser Thr Ala Met Asp Thr Leu Ser Ser Leu Val Phe Gln Leu
            1170                1175                1180
Gly Lys Lys Tyr Gln Ile Phe Ile Pro Met Val Asn Lys Val Leu Val
1185                1190                1195                1200
Arg His Arg Ile Asn His Gln Arg Tyr Asp Val Leu Ile Cys Arg Ile
            1205                1210                1215
Val Lys Gly Tyr Thr Leu Ala Asp Glu Glu Asp Pro Leu Ile Tyr
            1220                1225                1230
Gln His Arg Met Leu Arg Ser Ser Gln Gly Asp Ala Leu Ala Ser Gly
            1235                1240                1245
Pro Val Glu Thr Gly Pro Met Lys Lys Leu His Val Ser Thr Ile Asn
            1250                1255                1260
Leu Gln Lys Ala Trp Gly Ala Ala Arg Arg Val Ser Lys Asp Asp Trp
1265                1270                1275                1280
Leu Glu Trp Leu Arg Arg Leu Ser Leu Glu Leu Leu Lys Asp Ser Ser
            1285                1290                1295
Ser Pro Ser Leu Arg Ser Cys Trp Ala Leu Ala Gln Ala Tyr Asn Pro
            1300                1305                1310
Met Ala Arg Asp Leu Phe Asn Ala Ala Phe Val Ser Cys Trp Ser Glu
            1315                1320                1325
Leu Asn Glu Asp Gln Gln Asp Glu Leu Ile Arg Ser Ile Glu Leu Ala
            1330                1335                1340
Leu Thr Ser Gln Asp Ile Ala Glu Val Thr Gln Thr Leu Leu Asn Leu
1345                1350                1355                1360
Ala Glu Phe Met Glu His Ser Asp Lys Gly Pro Leu Pro Leu Arg Asp
            1365                1370                1375
Asp Asn Gly Ile Val Leu Leu Gly Glu Arg Ala Ala Lys Cys Arg Ala
            1380                1385                1390
Tyr Ala Lys Ala Leu His Tyr Lys Glu Leu Glu Phe Gln Lys Gly Pro
            1395                1400                1405
Thr Pro Ala Ile Leu Glu Ser Leu Ile Ser Ile Asn Asn Lys Leu Gln
            1410                1415                1420
Gln Pro Glu Ala Ala Ser Gly Val Leu Glu Tyr Ala Met Lys His Phe
1425                1430                1435                1440
Gly Glu Leu Glu Ile Gln Ala Thr Trp Tyr Glu Lys Leu His Glu Trp
            1445                1450                1455
Glu Asp Ala Leu Val Ala Tyr Asp Lys Lys Met Asp Thr Asn Lys Asp
            1460                1465                1470
Asp Pro Glu Leu Met Leu Gly Arg Met Arg Cys Leu Glu Ala Leu Gly
            1475                1480                1485
Glu Trp Gly Gln Leu His Gln Gln Cys Cys Glu Lys Trp Thr Leu Val
            1490                1495                1500
Asn Asp Glu Thr Gln Ala Lys Met Ala Arg Met Ala Ala Ala Ala
1505                1510                1515                1520
Trp Gly Leu Gly Gln Trp Asp Ser Met Glu Glu Tyr Thr Cys Met Ile
            1525                1530                1535
```

-continued

```
Pro Arg Asp Thr His Asp Gly Ala Phe Tyr Arg Ala Val Leu Ala Leu
            1540                1545                1550

His Gln Asp Leu Phe Ser Leu Ala Gln Gln Cys Ile Asp Lys Ala Arg
            1555                1560                1565

Asp Leu Leu Asp Ala Glu Leu Thr Ala Met Ala Gly Glu Ser Tyr Ser
    1570                1575                1580

Arg Ala Tyr Gly Ala Met Val Ser Cys His Met Leu Ser Glu Leu Glu
1585                1590                1595                1600

Glu Val Ile Gln Tyr Lys Leu Val Pro Glu Arg Arg Glu Ile Ile Arg
            1605                1610                1615

Gln Ile Trp Trp Glu Arg Leu Gln Gly Cys Gln Arg Ile Val Glu Asp
            1620                1625                1630

Trp Gln Lys Ile Leu Met Val Arg Ser Leu Val Val Ser Pro His Glu
            1635                1640                1645

Asp Met Arg Thr Trp Leu Lys Tyr Ala Ser Leu Cys Gly Lys Ser Gly
            1650                1655                1660

Arg Leu Ala Leu Ala His Lys Thr Leu Val Leu Leu Leu Gly Val Asp
1665                1670                1675                1680

Pro Ser Arg Gln Leu Asp His Pro Leu Pro Thr Val His Pro Gln Val
            1685                1690                1695

Thr Tyr Ala Tyr Met Lys Asn Met Trp Lys Ser Ala Arg Lys Ile Asp
            1700                1705                1710

Ala Phe Gln His Met Gln His Phe Val Gln Thr Met Gln Gln Gln Ala
            1715                1720                1725

Gln His Ala Ile Ala Thr Glu Asp Gln Gln His Lys Gln Glu Leu His
            1730                1735                1740

Lys Leu Met Ala Arg Cys Phe Leu Lys Leu Gly Glu Trp Gln Leu Asn
1745                1750                1755                1760

Leu Gln Gly Ile Asn Glu Ser Thr Ile Pro Lys Val Leu Gln Tyr Tyr
            1765                1770                1775

Ser Ala Ala Thr Glu His Asp Arg Ser Trp Tyr Lys Ala Trp His Ala
            1780                1785                1790

Trp Ala Val Met Asn Phe Glu Ala Val Leu His Tyr Lys His Gln Asn
            1795                1800                1805

Gln Ala Arg Asp Glu Lys Lys Lys Leu Arg His Ala Ser Gly Ala Asn
            1810                1815                1820

Ile Thr Asn Ala Thr Thr Thr Ala Thr Ala Ala Ser Ala Ala Ala
1825                1830                1835                1840

Ala Thr Ser Thr Glu Gly Ser Asn Ser Glu Ser Glu Ala Glu Ser Asn
            1845                1850                1855

Glu Ser Ser Pro Thr Pro Ser Pro Leu Gln Lys Lys Val Thr Glu Asp
            1860                1865                1870

Leu Ser Lys Thr Leu Leu Leu Tyr Thr Val Pro Ala Val Gln Gly Phe
            1875                1880                1885

Phe Arg Ser Ile Ser Leu Ser Arg Gly Asn Asn Leu Gln Asp Thr Leu
    1890                1895                1900

Arg Val Leu Thr Leu Trp Phe Asp Tyr Gly His Trp Pro Asp Val Asn
1905                1910                1915                1920

Glu Ala Leu Val Glu Gly Val Lys Ala Ile Gln Ile Asp Thr Trp Leu
            1925                1930                1935

Gln Val Ile Pro Gln Leu Ile Ala Arg Ile Asp Thr Pro Arg Pro Leu
            1940                1945                1950

Val Gly Arg Leu Ile His Gln Leu Leu Thr Asp Ile Gly Arg Tyr His
```

-continued

```
              1955                1960                1965
Pro Gln Ala Leu Ile Tyr Pro Leu Thr Val Ala Ser Lys Ser Thr Thr
         1970                1975                1980

Thr Ala Arg His Asn Ala Ala Asn Lys Ile Leu Lys Asn Met Cys Glu
1985                1990                1995                2000

His Ser Asn Thr Leu Val Gln Gln Ala Met Met Val Ser Glu Glu Leu
              2005                2010                2015

Ile Arg Val Ala Ile Leu Trp His Glu Met Trp His Glu Gly Leu Glu
         2020                2025                2030

Glu Ala Ser Arg Leu Tyr Phe Gly Glu Arg Asn Val Lys Gly Met Phe
              2035                2040                2045

Glu Val Leu Glu Pro Leu His Ala Met Met Glu Arg Gly Pro Gln Thr
         2050                2055                2060

Leu Lys Glu Thr Ser Phe Asn Gln Ala Tyr Gly Arg Asp Leu Met Glu
2065                2070                2075                2080

Ala Gln Glu Trp Cys Arg Lys Tyr Met Lys Ser Gly Asn Val Lys Asp
              2085                2090                2095

Leu Thr Gln Ala Trp Asp Leu Tyr Tyr His Val Phe Arg Arg Ile Ser
         2100                2105                2110

Lys Gln Leu Pro Gln Leu Thr Ser Leu Glu Leu Gln Tyr Val Ser Pro
              2115                2120                2125

Lys Leu Leu Met Cys Arg Asp Leu Glu Leu Ala Val Pro Gly Thr Tyr
              2130                2135                2140

Asp Pro Asn Gln Thr Ile Ile Arg Ile Gln Ser Ile Ala Pro Ser Leu
2145                2150                2155                2160

Gln Val Ile Thr Ser Lys Gln Arg Pro Arg Lys Leu Thr Leu Met Gly
              2165                2170                2175

Ser Asn Gly His Glu Phe Val Phe Leu Leu Lys Gly His Glu Asp Leu
              2180                2185                2190

Arg Gln Asp Glu Arg Val Met Gln Leu Phe Gly Leu Val Asn Thr Leu
         2195                2200                2205

Leu Ala Asn Asp Pro Thr Ser Leu Arg Lys Asn Leu Ser Ile Gln Arg
         2210                2215                2220

Tyr Ala Val Ile Pro Leu Ser Thr Asn Ser Gly Leu Ile Gly Trp Val
2225                2230                2235                2240

Pro His Cys Asp Thr Leu His Ala Leu Ile Arg Asp Tyr Arg Glu Lys
              2245                2250                2255

Lys Lys Ile Leu Leu Asn Ile Glu His Arg Ile Met Leu Arg Met Ala
              2260                2265                2270

Pro Asp Tyr Asp His Leu Thr Leu Met Gln Lys Val Glu Val Phe Glu
              2275                2280                2285

His Ala Val Asn Asn Thr Ala Gly Asp Asp Leu Ala Lys Leu Leu Trp
              2290                2295                2300

Leu Lys Ser Pro Ser Ser Glu Val Trp Phe Asp Arg Arg Thr Asn Tyr
2305                2310                2315                2320

Thr Arg Ser Leu Ala Val Met Ser Met Val Gly Tyr Ile Leu Gly Leu
              2325                2330                2335

Gly Asp Arg His Pro Ser Asn Leu Met Leu Asp Arg Leu Ser Gly Lys
              2340                2345                2350

Ile Leu His Ile Asp Phe Gly Asp Cys Phe Glu Val Ala Met Thr Arg
              2355                2360                2365

Glu Lys Phe Pro Glu Lys Ile Pro Phe Arg Leu Thr Arg Met Leu Thr
         2370                2375                2380
```

```
Asn Ala Met Glu Val Thr Gly Leu Asp Arg Asn Tyr Arg Thr Thr Cys
2385                2390                2395                2400

His Thr Val Met Glu Val Leu Arg Glu His Lys Asp Ser Val Met Ala
            2405                2410                2415

Val Leu Glu Ala Phe Val Tyr Asp Pro Leu Leu Asn Trp Arg Leu Met
        2420                2425                2430

Asp Thr Asn Ala Lys Gly Asn Lys Arg Ser Arg Thr Arg Thr Asp Ser
            2435                2440                2445

Tyr Ser Ala Gly Gln Ser Val Glu Ile Leu Asp Gly Val Glu Leu Gly
    2450                2455                2460

Glu Pro Ala His Lys Lys Thr Gly Thr Thr Val Pro Glu Ser Ile His
2465                2470                2475                2480

Ser Phe Ile Gly Asp Gly Leu Val Lys Pro Glu Ala Leu Asn Lys Lys
                2485                2490                2495

Ala Ile Gln Ile Ile Asn Arg Val Arg Asp Lys Leu Thr Gly Arg Asp
            2500                2505                2510

Phe Ser His Asp Asp Thr Leu Asp Val Pro Thr Gln Val Glu Leu Leu
        2515                2520                2525

Ile Lys Gln Ala Thr Ser His Glu Asn Leu Cys Gln Cys Tyr Ile Gly
        2530                2535                2540

Trp Cys Pro Phe Trp
2545

(2) INFORMATION FOR SEQ ID NO:2:

(i) SEQUENCE CHARACTERISTICS:
        (A) LENGTH: 2470 amino acids
        (B) TYPE: amino acid
        (D) TOPOLOGY: linear (ii) MOLECULE TYPE: protein (vi) ORIGINAL SOURCE:
        (A) ORGANISM: Saccharomyces cerevisiae (xi) SEQUENCE DESCRIPTION: SEQ ID NO:2:

Met Glu Pro His Glu Glu Gln Ile Trp Lys Ser Lys Leu Leu Lys Ala
1               5                  10                  15

Ala Asn Asn Asp Met Asp Met Asp Arg Asn Val Pro Leu Ala Pro Asn
                20                  25                  30

Leu Asn Val Asn Met Asn Met Lys Met Asn Ala Ser Arg Asn Gly Asp
            35                  40                  45

Glu Phe Gly Leu Thr Ser Ser Arg Phe Gly Gly Val Val Ile Gly Ser
50                  55                  60

Asn Gly Asp Val Asn Phe Lys Pro Ile Leu Glu Lys Ile Phe Arg Glu
65                  70                  75                  80

Leu Thr Ser Asp Tyr Lys Glu Glu Arg Lys Leu Ala Ser Ile Ser Leu
                85                  90                  95

Phe Asp Leu Leu Val Ser Leu Glu His Glu Leu Ser Ile Glu Glu Phe
            100                 105                 110

Gln Ala Ile Ser Asn Asp Ile Asn Asn Lys Ile Leu Glu Leu Val His
            115                 120                 125

Thr Lys Lys Thr Asn Thr Arg Val Gly Ala Val Leu Ser Ile Asp Thr
    130                 135                 140

Leu Ile Ser Phe Tyr Ala Tyr Thr Glu Arg Leu Pro Asn Glu Thr Ser
145                 150                 155                 160
```

-continued

```
Arg Leu Ala Gly Tyr Leu Arg Gly Leu Ile Pro Ser Asn Asp Val Glu
                165                 170                 175

Val Met Arg Leu Ala Ala Lys Thr Leu Gly Lys Leu Ala Val Pro Gly
            180                 185                 190

Gly Thr Tyr Thr Ser Asp Phe Val Glu Phe Glu Ile Lys Ser Cys Leu
        195                 200                 205

Glu Trp Leu Thr Ala Ser Thr Glu Lys Asn Ser Phe Ser Ser Ser Lys
    210                 215                 220

Pro Asp His Ala Lys His Ala Ala Leu Ile Ile Thr Ala Leu Ala
225                 230                 235                 240

Glu Asn Cys Pro Tyr Leu Leu Tyr Gln Tyr Leu Asn Ser Ile Leu Asp
                245                 250                 255

Asn Ile Trp Arg Ala Leu Arg Asp Pro His Leu Val Ile Arg Ile Asp
            260                 265                 270

Ala Ser Ile Thr Leu Ala Lys Cys Leu Ser Thr Leu Arg Asn Arg Asp
        275                 280                 285

Pro Gln Leu Thr Ser Gln Trp Val Gln Arg Leu Ala Thr Ser Cys Glu
    290                 295                 300

Tyr Gly Phe Gln Val Asn Thr Leu Glu Cys Ile His Ala Ser Leu Leu
305                 310                 315                 320

Val Tyr Lys Glu Ile Leu Phe Leu Lys Asp Pro Phe Leu Asn Gln Val
                325                 330                 335

Phe Asp Gln Met Cys Leu Asn Cys Ile Ala Tyr Glu Asn His Lys Ala
            340                 345                 350

Lys Met Ile Arg Glu Lys Ile Tyr Gln Ile Val Pro Leu Leu Ala Ser
        355                 360                 365

Phe Asn Pro Gln Leu Phe Ala Gly Lys Tyr Leu His Gln Ile Met Asp
    370                 375                 380

Asn Tyr Leu Glu Ile Leu Thr Asn Ala Pro Ala Lys Lys Ile Pro His
385                 390                 395                 400

Leu Lys Asp Asp Lys Pro Gln Ile Leu Ile Ser Ile Gly Asp Ile Ala
                405                 410                 415

Tyr Glu Val Gly Pro Asp Ile Ala Pro Tyr Val Lys Gln Ile Leu Asp
            420                 425                 430

Tyr Ile Glu His Asp Leu Gln Thr Lys Phe Lys Phe Arg Lys Lys Phe
        435                 440                 445

Glu Asn Glu Ile Phe Tyr Cys Ile Gly Arg Leu Ala Val Pro Leu Gly
    450                 455                 460

Pro Val Leu Gly Lys Leu Leu Asn Arg Asn Ile Leu Asp Leu Met Phe
465                 470                 475                 480

Lys Cys Pro Leu Ser Asp Tyr Met Gln Glu Thr Phe Gln Ile Leu Thr
                485                 490                 495

Glu Arg Ile Pro Ser Leu Gly Pro Lys Ile Asn Asp Glu Leu Leu Asn
            500                 505                 510

Leu Val Cys Ser Thr Leu Ser Gly Thr Pro Phe Ile Gln Pro Gly Ser
        515                 520                 525

Pro Met Glu Ile Pro Ser Phe Ser Arg Glu Arg Ala Arg Glu Trp Arg
    530                 535                 540

Asn Lys Ser Ile Leu Gln Lys Thr Gly Glu Ser Asn Asp Asp Asn
545                 550                 555                 560

Asp Ile Lys Ile Ile Gln Ala Phe Arg Met Leu Lys Asn Ile Lys
                565                 570                 575

Ser Arg Phe Ser Leu Val Glu Phe Val Arg Ile Val Ala Leu Ser Tyr
```

-continued

```
                    580                 585                 590
Ile Glu His Thr Asp Pro Arg Val Arg Lys Leu Ala Ala Leu Thr Ser
                595                 600                 605
Cys Glu Ile Tyr Val Lys Asp Asn Ile Cys Lys Gln Thr Ser Leu His
            610                 615                 620
Ser Leu Asn Thr Val Ser Glu Val Leu Ser Lys Leu Leu Ala Ile Thr
625                 630                 635                 640
Ile Ala Asp Pro Leu Gln Asp Ile Arg Leu Glu Val Leu Lys Asn Leu
                    645                 650                 655
Asn Pro Cys Phe Asp Pro Gln Leu Ala Gln Pro Asp Asn Leu Arg Leu
                660                 665                 670
Leu Phe Thr Ala Leu His Asp Glu Ser Phe Asn Ile Gln Ser Val Ala
            675                 680                 685
Met Glu Leu Val Gly Arg Leu Ser Ser Val Asn Pro Ala Tyr Val Ile
            690                 695                 700
Pro Ser Ile Arg Lys Ile Leu Glu Leu Leu Thr Lys Leu Lys Phe
705                 710                 715                 720
Ser Thr Ser Ser Arg Glu Lys Glu Glu Thr Ala Ser Leu Leu Cys Thr
                725                 730                 735
Leu Ile Arg Ser Ser Lys Asp Val Ala Lys Pro Tyr Ile Glu Pro Leu
                740                 745                 750
Leu Asn Val Leu Leu Pro Lys Phe Gln Asp Thr Ser Ser Thr Val Ala
                755                 760                 765
Ser Thr Ala Leu Arg Thr Ile Gly Glu Leu Ser Val Val Gly Gly Glu
770                 775                 780
Asp Met Lys Ile Tyr Leu Lys Asp Leu Phe Pro Leu Ile Ile Lys Thr
785                 790                 795                 800
Phe Gln Asp Gln Ser Asn Ser Phe Lys Arg Glu Ala Ala Leu Lys Ala
                805                 810                 815
Leu Gly Gln Leu Ala Ala Ser Ser Gly Tyr Val Ile Asp Pro Leu Leu
                820                 825                 830
Asp Tyr Pro Glu Leu Leu Gly Ile Leu Val Asn Ile Leu Lys Thr Glu
            835                 840                 845
Asn Ser Gln Asn Ile Arg Arg Gln Thr Val Thr Leu Ile Gly Ile Leu
850                 855                 860
Gly Ala Ile Asp Pro Tyr Arg Gln Lys Glu Arg Glu Val Thr Ser Thr
865                 870                 875                 880
Thr Asp Ile Ser Thr Glu Gln Asn Ala Pro Pro Ile Asp Ile Ala Leu
                885                 890                 895
Leu Met Gln Gly Met Ser Pro Ser Asn Asp Glu Tyr Tyr Thr Thr Val
                900                 905                 910
Val Ile His Cys Leu Leu Lys Ile Leu Lys Asp Pro Ser Leu Ser Ser
            915                 920                 925
Tyr His Thr Ala Val Ile Gln Ala Ile Met His Ile Phe Gln Thr Leu
        930                 935                 940
Gly Leu Lys Cys Val Ser Phe Leu Asp Gln Ile Pro Thr Ile Leu
945                 950                 955                 960
Asp Val Met Arg Thr Cys Ser Gln Ser Leu Leu Glu Phe Tyr Phe Gln
                965                 970                 975
Gln Leu Cys Ser Leu Ile Ile Val Arg Gln His Ile Arg Pro His
                980                 985                 990
Val Asp Ser Ile Phe Gln Ala Ile Lys Asp Phe Ser Ser Val Ala Lys
            995                 1000                1005
```

-continued

```
Leu Gln Ile Thr Leu Val Ser Val Ile Glu Ala Ile Ser Lys Ala Leu
    1010                1015                1020
Glu Gly Glu Phe Lys Arg Leu Val Pro Leu Thr Leu Thr Leu Phe Leu
1025                1030                1035                1040
Val Ile Leu Glu Asn Asp Lys Ser Ser Asp Lys Val Leu Ser Arg Arg
                1045                1050                1055
Val Leu Arg Leu Leu Glu Ser Phe Gly Pro Asn Leu Glu Gly Tyr Ser
                1060                1065                1070
His Leu Ile Thr Pro Lys Ile Val Gln Met Ala Glu Phe Thr Ser Gly
            1075                1080                1085
Asn Leu Gln Arg Ser Ala Ile Ile Thr Ile Gly Lys Leu Ala Lys Asp
    1090                1095                1100
Val Asp Leu Phe Glu Met Ser Ser Arg Ile Val His Ser Leu Leu Arg
1105                1110                1115                1120
Val Leu Ser Ser Thr Thr Ser Asp Glu Leu Ser Lys Val Ile Met Asn
                1125                1130                1135
Thr Leu Ser Leu Leu Leu Ile Gln Met Gly Thr Ser Phe Ala Ile Phe
            1140                1145                1150
Ile Pro Val Ile Asn Glu Val Leu Met Lys Lys His Ile Gln His Thr
        1155                1160                1165
Ile Tyr Asp Asp Leu Thr Asn Arg Ile Leu Asn Asn Asp Val Leu Pro
    1170                1175                1180
Thr Lys Ile Leu Glu Ala Asn Thr Thr Asp Tyr Lys Pro Ala Glu Gln
1185                1190                1195                1200
Met Glu Ala Ala Asp Ala Gly Val Ala Lys Leu Pro Ile Asn Gln Ser
                1205                1210                1215
Val Leu Lys Ser Ala Trp Asn Ser Ser Gln Gln Arg Thr Lys Glu Asp
                1220                1225                1230
Trp Gln Glu Trp Ser Lys Arg Leu Ser Ile Gln Leu Leu Lys Glu Ser
            1235                1240                1245
Pro Ser His Ala Leu Arg Ala Cys Ser Asn Leu Ala Ser Met Tyr Tyr
    1250                1255                1260
Pro Leu Ala Lys Glu Leu Phe Asn Thr Ala Phe Ala Cys Val Trp Thr
1265                1270                1275                1280
Glu Leu Tyr Ser Gln Tyr Gln Glu Asp Leu Ile Gly Ser Leu Cys Ile
                1285                1290                1295
Ala Leu Ser Ser Pro Leu Asn Pro Pro Glu Ile His Gln Thr Leu Leu
            1300                1305                1310
Asn Leu Val Glu Phe Met Glu His Asp Asp Lys Ala Leu Pro Ile Pro
        1315                1320                1325
Thr Gln Ser Leu Gly Glu Tyr Ala Glu Arg Cys His Ala Tyr Ala Lys
    1330                1335                1340
Ala Leu His Tyr Lys Glu Ile Lys Phe Ile Lys Glu Pro Glu Asn Ser
1345                1350                1355                1360
Thr Ile Glu Ser Leu Ile Ser Ile Asn Asn Gln Leu Asn Gln Thr Asp
                1365                1370                1375
Ala Ala Ile Gly Ile Leu Lys His Ala Gln Gln His His Ser Leu Gln
            1380                1385                1390
Leu Lys Glu Thr Trp Phe Glu Lys Leu Glu Arg Trp Glu Asp Ala Leu
        1395                1400                1405
His Ala Tyr Asn Glu Arg Glu Lys Ala Gly Asp Thr Ser Val Ser Val
    1410                1415                1420
```

-continued

```
Thr Leu Gly Lys Met Arg Ser Leu His Ala Leu Gly Glu Trp Glu Gln
1425                1430                1435                1440

Leu Ser Gln Leu Ala Ala Arg Lys Trp Lys Val Ser Lys Leu Gln Thr
            1445                1450                1455

Lys Lys Leu Ile Ala Pro Leu Ala Ala Gly Ala Arg Trp Gly Leu Gly
            1460                1465                1470

Glu Trp Asp Met Leu Glu Gln Tyr Ile Ser Val Met Lys Pro Lys Ser
        1475                1480                1485

Pro Asp Lys Glu Phe Phe Asp Ala Ile Leu Tyr Leu His Lys Asn Asp
        1490                1495                1500

Tyr Asp Asn Ala Ser Lys His Ile Leu Asn Ala Arg Asp Leu Leu Val
1505                1510                1515                1520

Thr Glu Ile Ser Ala Leu Ile Asn Glu Ser Tyr Asn Arg Ala Tyr Ser
                1525                1530                1535

Val Ile Val Arg Thr Gln Ile Ile Thr Glu Phe Glu Glu Ile Ile Lys
            1540                1545                1550

Tyr Lys Gln Leu Pro Pro Asn Ser Glu Lys Lys Leu His Tyr Gln Asn
            1555                1560                1565

Leu Trp Thr Lys Arg Leu Leu Gly Cys Gln Lys Asn Val Asp Leu Trp
        1570                1575                1580

Gln Arg Val Leu Arg Val Arg Ser Leu Val Ile Lys Pro Lys Gln Asp
1585                1590                1595                1600

Leu Gln Ile Trp Ile Lys Phe Ala Asn Leu Cys Arg Lys Ser Gly Arg
                1605                1610                1615

Met Arg Leu Ala Asn Lys Ala Leu Asn Met Leu Leu Glu Gly Gly Asn
            1620                1625                1630

Asp Pro Ser Leu Pro Asn Thr Val Lys Ala Pro Pro Val Val Tyr
            1635                1640                1645

Ala Gln Leu Lys Tyr Ile Trp Ala Thr Gly Ala Tyr Lys Glu Ala Leu
    1650                1655                1660

Asn His Leu Ile Gly Phe Thr Ser Arg Leu Ala His Asp Leu Gly Leu
1665                1670                1675                1680

Asp Pro Asn Asn Met Ile Ala Gln Ser Val Lys Leu Ser Ser Ala Ser
            1685                1690                1695

Thr Ala Pro Tyr Val Glu Glu Tyr Thr Lys Leu Leu Ala Arg Cys Phe
        1700                1705                1710

Leu Lys Gln Gly Glu Trp Arg Ile Ala Thr Gln Pro Asn Trp Arg Asn
        1715                1720                1725

Thr Asn Pro Asp Ala Ile Leu Gly Ser Tyr Leu Leu Ala Thr His Phe
        1730                1735                1740

Asp Lys Asn Trp Tyr Lys Ala Trp His Asn Trp Ala Leu Ala Asn Phe
1745                1750                1755                1760

Glu Val Ile Ser Met Val Gln Glu Glu Thr Lys Leu Asn Gly Gly Lys
            1765                1770                1775

Asn Asp Asp Asp Asp Asp Thr Ala Val Asn Asn Asp Asn Val Arg Ile
            1780                1785                1790

Asp Gly Ser Ile Leu Gly Ser Gly Ser Leu Thr Ile Asn Gly Asn Arg
        1795                1800                1805

Tyr Pro Leu Glu Leu Ile Gln Arg His Val Val Pro Ala Ile Lys Gly
        1810                1815                1820

Phe Phe His Ser Ile Ser Leu Leu Glu Thr Ser Cys Leu Gln Asp Thr
1825                1830                1835                1840

Leu Arg Leu Leu Thr Leu Leu Phe Asn Phe Gly Gly Ile Lys Glu Val
```

-continued

```
                  1845                1850               1855

Ser Gln Ala Met Tyr Glu Gly Phe Asn Leu Met Lys Ile Glu Asn Trp
            1860                1865              1870

Leu Glu Val Leu Pro Gln Leu Ile Ser Arg Ile His Gln Pro Asp Pro
        1875                1880                1885

Thr Val Ser Asn Ser Leu Leu Ser Leu Leu Ser Asp Leu Gly Lys Ala
        1890                1895                1900

His Pro Gln Ala Leu Val Tyr Pro Leu Thr Val Ala Ile Lys Ser Glu
1905                1910                1915                1920

Ser Val Ser Arg Gln Lys Ala Ala Leu Ser Ile Ile Glu Lys Ile Arg
                1925                1930                1935

Ile His Ser Pro Val Leu Val Asn Gln Ala Glu Leu Val Ser His Glu
            1940                1945                1950

Leu Ile Arg Val Ala Val Leu Trp His Glu Leu Trp Tyr Glu Gly Leu
        1955                1960                1965

Glu Asp Ala Arg Arg Gln Phe Phe Val Glu His Asn Ile Glu Lys Met
1970                1975                1980

Phe Ser Thr Leu Glu Pro Leu His Lys His Leu Gly Asn Glu Pro Gln
1985                1990                1995                2000

Thr Leu Ser Glu Val Ser Phe Gln Lys Ser Phe Gly Arg Asp Leu Asn
            2005                2010                2015

Asp Ala Tyr Glu Trp Leu Asn Asn Tyr Lys Lys Ser Lys Asp Ile Asn
        2020                2025                2030

Asn Leu Asn Gln Ala Trp Asp Ile Tyr Tyr Asn Val Phe Arg Lys Ile
        2035                2040                2045

Thr Arg Gln Ile Pro Gln Leu Gln Thr Leu Asp Leu Gln His Val Ser
        2050                2055                2060

Pro Gln Leu Leu Ala Thr His Asp Leu Glu Leu Ala Val Pro Gly Thr
2065                2070                2075                2080

Tyr Phe Pro Gly Lys Pro Thr Ile Arg Ile Ala Lys Phe Glu Pro Leu
            2085                2090                2095

Phe Ser Val Ile Ser Ser Lys Gln Arg Pro Arg Lys Phe Ser Ile Lys
        2100                2105                2110

Gly Ser Asp Gly Lys Asp Tyr Lys Tyr Val Leu Lys Gly His Glu Asp
        2115                2120                2125

Ile Arg Gln Asp Ser Leu Val Met Gln Leu Phe Gly Leu Val Asn Thr
    2130                2135                2140

Leu Leu Lys Asn Asp Ser Glu Cys Phe Lys Arg His Leu Asp Ile Gln
2145                2150                2155                2160

Gln Tyr Pro Ala Ile Pro Leu Ser Pro Lys Ser Gly Leu Leu Gly Trp
            2165                2170                2175

Val Pro Asn Ser Asp Thr Phe His Val Leu Ile Arg Glu His Arg Asp
        2180                2185                2190

Ala Lys Lys Ile Pro Leu Asn Ile Glu Gln Trp Val Met Leu Gln Met
        2195                2200                2205

Ala Pro Asp Tyr Glu Asn Leu Thr Leu Leu Gln Lys Ile Glu Val Phe
        2210                2215                2220

Thr Tyr Ala Leu Asp Asn Thr Lys Gly Gln Asp Leu Tyr Lys Ile Leu
2225                2230                2235                2240

Trp Leu Lys Ser Arg Ser Ser Glu Thr Trp Leu Glu Arg Arg Thr Thr
                2245                2250                2255

Tyr Thr Arg Ser Leu Ala Val Met Ser Met Thr Gly Tyr Ile Leu Gly
            2260                2265                2270
```

-continued

```
Leu Gly Asp Arg His Pro Ser Asn Leu Met Leu Asp Arg Ile Thr Gly
        2275                2280                2285

Lys Val Ile His Ile Asp Phe Gly Asp Cys Phe Glu Ala Ala Ile Leu
        2290                2295                2300

Arg Glu Lys Tyr Pro Glu Lys Val Pro Phe Arg Leu Thr Arg Met Leu
2305                2310                2315                2320

Thr Tyr Ala Met Glu Val Ser Gly Ile Glu Gly Ser Phe Arg Ile Thr
                2325                2330                2335

Cys Glu Asn Val Met Arg Val Leu Arg Asp Asn Lys Glu Ser Leu Met
            2340                2345                2350

Ala Ile Leu Glu Ala Phe Ala Leu Asp Pro Leu Ile His Trp Gly Phe
        2355                2360                2365

Asp Leu Pro Pro Gln Lys Leu Thr Glu Gln Thr Gly Ile Pro Leu Pro
    2370                2375                2380

Leu Ile Asn Pro Ser Glu Leu Leu Arg Lys Gly Ala Ile Thr Val Glu
2385                2390                2395                2400

Glu Ala Ala Asn Met Glu Ala Glu Gln Gln Asn Glu Thr Arg Asn Ala
                2405                2410                2415

Arg Ala Met Leu Val Leu Arg Arg Ile Thr Asp Lys Leu Thr Gly Asn
            2420                2425                2430

Asp Ile Lys Arg Phe Asn Glu Leu Asp Val Pro Glu Gln Val Asp Lys
        2435                2440                2445

Leu Ile Gln Gln Ala Thr Ser Ile Glu Arg Leu Cys Gln His Tyr Ile
    2450                2455                2460

Gly Trp Cys Pro Phe Trp
2465                2470

(2) INFORMATION FOR SEQ ID NO:3:

(i) SEQUENCE CHARACTERISTICS:
        (A) LENGTH: 2474 amino acids
        (B) TYPE: amino acid
        (D) TOPOLOGY: linear (ii) MOLECULE TYPE: protein (vi) ORIGINAL SOURCE:
        (A) ORGANISM: Saccharomyces cerevisiae (xi) SEQUENCE DESCRIPTION: SEQ ID NO:3:

Met Asn Lys Tyr Ile Asn Lys Tyr Thr Thr Pro Pro Asn Leu Leu Ser
1               5                   10                  15

Leu Arg Gln Arg Ala Glu Gly Lys His Arg Thr Arg Lys Lys Leu Thr
            20                  25                  30

His Lys Ser His Ser His Asp Asp Glu Met Ser Thr Thr Ser Asn Thr
        35                  40                  45

Asp Ser Asn His Asn Gly Pro Asn Asp Ser Gly Arg Val Ile Thr Gly
    50                  55                  60

Ser Ala Gly His Ile Gly Lys Ile Ser Phe Val Asp Ser Glu Leu Asp
65                  70                  75                  80

Thr Thr Phe Ser Thr Leu Asn Leu Ile Phe Asp Lys Leu Lys Ser Asp
                85                  90                  95

Val Pro Gln Glu Arg Ala Ser Gly Ala Asn Glu Leu Ser Thr Thr Leu
            100                 105                 110

Thr Ser Leu Ala Arg Glu Val Ser Ala Glu Gln Phe Gln Arg Phe Ser
        115                 120                 125
```

-continued

```
Asn Ser Leu Asn Asn Lys Ile Phe Glu Leu Ile His Gly Phe Thr Ser
        130                 135                 140
Ser Glu Lys Ile Gly Gly Ile Leu Ala Val Asp Thr Leu Ile Ser Phe
145                 150                 155                 160
Tyr Leu Ser Thr Glu Glu Leu Pro Asn Gln Thr Ser Arg Leu Ala Asn
                165                 170                 175
Tyr Leu Arg Val Leu Ile Pro Ser Ser Asp Ile Glu Val Met Arg Leu
            180                 185                 190
Ala Ala Asn Thr Leu Gly Arg Leu Thr Val Pro Gly Gly Thr Leu Thr
        195                 200                 205
Ser Asp Phe Val Glu Phe Glu Val Arg Thr Cys Ile Asp Trp Leu Thr
    210                 215                 220
Leu Thr Ala Asp Asn Asn Ser Ser Ser Lys Leu Glu Tyr Arg Arg
225                 230                 235                 240
His Ala Ala Leu Leu Ile Ile Lys Ala Leu Ala Asp Asn Ser Pro Tyr
                245                 250                 255
Leu Leu Tyr Pro Tyr Val Asn Ser Ile Leu Asp Asn Ile Trp Val Pro
            260                 265                 270
Leu Arg Asp Ala Lys Leu Ile Ile Arg Leu Asp Ala Ala Val Ala Leu
        275                 280                 285
Gly Lys Cys Leu Thr Ile Ile Gln Asp Arg Asp Pro Ala Leu Gly Lys
    290                 295                 300
Gln Trp Phe Gln Arg Leu Phe Gln Gly Cys Thr His Gly Leu Ser Leu
305                 310                 315                 320
Asn Thr Asn Asp Ser Val His Ala Thr Leu Val Phe Arg Glu Leu
                325                 330                 335
Leu Ser Leu Lys Ala Pro Tyr Leu Arg Asp Lys Tyr Asp Asp Ile Tyr
            340                 345                 350
Lys Ser Thr Met Lys Tyr Lys Glu Tyr Lys Phe Asp Val Ile Arg Arg
        355                 360                 365
Glu Val Tyr Ala Ile Leu Pro Leu Leu Ala Ala Phe Asp Pro Ala Ile
    370                 375                 380
Phe Thr Lys Lys Tyr Leu Asp Arg Ile Met Val His Tyr Leu Arg Tyr
385                 390                 395                 400
Leu Lys Asn Ile Asp Met Asn Ala Ala Asn Ser Asp Lys Pro Phe
                405                 410                 415
Ile Leu Val Ser Ile Gly Asp Ile Ala Phe Glu Val Gly Ser Ser Ile
            420                 425                 430
Ser Pro Tyr Met Thr Leu Ile Leu Asp Asn Ile Arg Glu Gly Leu Arg
        435                 440                 445
Thr Lys Phe Lys Val Arg Lys Gln Phe Glu Lys Asp Leu Phe Tyr Cys
    450                 455                 460
Ile Gly Lys Leu Ala Cys Ala Leu Gly Pro Ala Phe Ala Lys His Leu
465                 470                 475                 480
Asn Lys Asp Leu Leu Asn Leu Met Leu Asn Cys Pro Met Ser Asp His
                485                 490                 495
Met Gln Glu Thr Leu Met Ile Leu Asn Glu Lys Ile Pro Ser Leu Glu
            500                 505                 510
Ser Thr Val Asn Ser Arg Ile Leu Asn Leu Leu Ser Ile Ser Leu Ser
        515                 520                 525
Gly Glu Lys Phe Ile Gln Ser Asn Gln Tyr Asp Phe Asn Asn Gln Phe
    530                 535                 540
Ser Ile Glu Lys Ala Arg Lys Ser Arg Asn Gln Ser Phe Met Lys Lys
```

```
                545                 550                 555                 560

Thr Gly Glu Ser Asn Asp Asp Ile Thr Asp Ala Gln Ile Leu Ile Gln
                565                 570                 575

Cys Phe Lys Met Leu Gln Leu Ile His His Gln Tyr Ser Leu Thr Glu
                580                 585                 590

Phe Val Arg Leu Ile Thr Ile Ser Tyr Ile Glu His Glu Asp Ser Ser
                595                 600                 605

Val Arg Lys Leu Ala Ala Leu Thr Ser Cys Asp Leu Phe Ile Lys Asp
                610                 615                 620

Asp Ile Cys Lys Gln Thr Ser Val His Ala Leu His Ser Val Ser Glu
625                 630                 635                 640

Val Leu Ser Lys Leu Leu Met Ile Ala Ile Thr Asp Pro Val Ala Glu
                645                 650                 655

Ile Arg Leu Glu Ile Leu Gln His Leu Gly Ser Asn Phe Asp Pro Gln
                660                 665                 670

Leu Ala Gln Pro Asp Asn Leu Arg Leu Leu Phe Met Ala Leu Asn Asp
                675                 680                 685

Glu Ile Phe Gly Ile Gln Leu Glu Ala Ile Lys Ile Gly Arg Leu
                690                 695                 700

Ser Ser Val Asn Pro Ala Tyr Val Val Pro Ser Leu Arg Lys Thr Leu
705                 710                 715                 720

Leu Glu Leu Leu Thr Gln Leu Lys Phe Ser Asn Met Pro Lys Lys Lys
                725                 730                 735

Glu Glu Ser Ala Thr Leu Leu Cys Thr Leu Ile Asn Ser Ser Asp Glu
                740                 745                 750

Val Ala Lys Pro Tyr Ile Asp Pro Ile Leu Asp Val Ile Leu Pro Lys
                755                 760                 765

Cys Gln Asp Ala Ser Ser Ala Val Ala Ser Thr Ala Leu Lys Val Leu
                770                 775                 780

Gly Glu Leu Ser Val Val Gly Gly Lys Glu Met Thr Arg Tyr Leu Lys
785                 790                 795                 800

Glu Leu Met Pro Leu Ile Ile Asn Thr Phe Gln Asp Gln Ser Asn Ser
                805                 810                 815

Phe Lys Arg Asp Ala Ala Leu Thr Thr Leu Gly Gln Leu Ala Ala Ser
                820                 825                 830

Ser Gly Tyr Val Val Gly Pro Leu Leu Asp Tyr Pro Glu Leu Leu Gly
                835                 840                 845

Ile Leu Ile Asn Ile Leu Lys Thr Glu Asn Asn Pro His Ile Arg Arg
850                 855                 860

Gly Thr Val Arg Leu Ile Gly Ile Leu Gly Ala Leu Asp Pro Tyr Lys
865                 870                 875                 880

His Arg Glu Ile Glu Val Thr Ser Asn Ser Lys Ser Ser Val Glu Gln
                885                 890                 895

Asn Ala Pro Ser Ile Asp Ile Ala Leu Leu Met Gln Gly Val Ser Pro
                900                 905                 910

Ser Asn Asp Glu Tyr Tyr Pro Thr Val Val Ile His Asn Leu Met Lys
                915                 920                 925

Ile Leu Asn Asp Pro Ser Leu Ser Ile His His Thr Ala Ala Ile Gln
                930                 935                 940

Ala Ile Met His Ile Phe Gln Asn Leu Gly Leu Arg Cys Val Ser Phe
945                 950                 955                 960

Leu Asp Gln Ile Ile Pro Gly Ile Ile Leu Val Met Arg Ser Cys Pro
                965                 970                 975
```

-continued

```
Pro Ser Gln Leu Asp Phe Tyr Phe Gln Gln Leu Gly Ser Leu Ile Ser
        980                 985                 990
Ile Val Lys Gln His Ile Arg Pro His Val Glu Lys Ile Tyr Gly Val
        995                 1000                1005
Ile Arg Glu Phe Phe Pro Ile Ile Lys Leu Gln Ile Thr Ile Ile Ser
        1010                1015                1020
Val Ile Glu Ser Ile Ser Lys Ala Leu Glu Gly Glu Phe Lys Arg Phe
1025                1030                1035                1040
Val Pro Glu Thr Leu Thr Phe Phe Leu Asp Ile Leu Glu Asn Asp Gln
                    1045                1050                1055
Ser Asn Lys Arg Ile Val Pro Ile Arg Ile Leu Lys Ser Leu Val Thr
                    1060                1065                1070
Phe Gly Pro Asn Leu Glu Asp Tyr Ser His Leu Ile Met Pro Ile Val
                    1075                1080                1085
Val Arg Met Thr Glu Tyr Ser Ala Gly Ser Leu Lys Lys Ile Ser Ile
                    1090                1095                1100
Ile Thr Leu Gly Arg Leu Ala Lys Asn Ile Asn Leu Ser Glu Met Ser
1105                1110                1115                1120
Ser Arg Ile Val Gln Ala Leu Val Arg Ile Leu Asn Asn Gly Asp Arg
                    1125                1130                1135
Glu Leu Thr Lys Ala Thr Met Asn Thr Leu Ser Leu Leu Leu Leu Gln
                    1140                1145                1150
Leu Gly Thr Asp Phe Val Val Phe Val Pro Val Ile Asn Lys Ala Leu
                    1155                1160                1165
Leu Arg Asn Arg Ile Gln His Ser Val Tyr Asp Gln Leu Val Asn Lys
                    1170                1175                1180
Leu Leu Asn Asn Glu Cys Leu Pro Thr Asn Ile Ile Phe Asp Lys Glu
1185                1190                1195                1200
Asn Glu Val Pro Glu Arg Lys Asn Tyr Glu Asp Glu Met Gln Val Thr
                    1205                1210                1215
Lys Leu Pro Val Asn Gln Asn Ile Leu Lys Asn Ala Trp Tyr Cys Ser
                    1220                1225                1230
Gln Gln Lys Thr Lys Glu Asp Trp Gln Glu Trp Ile Arg Arg Leu Ser
                    1235                1240                1245
Ile Gln Leu Leu Lys Glu Ser Pro Ser Ala Cys Leu Arg Ser Cys Ser
1250                1255                1260
Ser Leu Val Ser Val Tyr Tyr Pro Leu Ala Arg Glu Leu Phe Asn Ala
1265                1270                1275                1280
Ser Phe Ser Ser Cys Trp Val Glu Leu Gln Thr Ser Tyr Gln Glu Asp
                    1285                1290                1295
Leu Ile Gln Ala Leu Cys Lys Ala Leu Ser Ser Ser Glu Asn Pro Pro
                    1300                1305                1310
Glu Ile Tyr Gln Met Leu Leu Asn Leu Val Glu Phe Met Glu His Asp
                    1315                1320                1325
Asp Lys Pro Leu Pro Ile Pro Ile His Thr Leu Gly Lys Tyr Ala Gln
1330                1335                1340
Lys Cys His Ala Phe Ala Lys Ala Leu His Tyr Lys Glu Val Glu Phe
1345                1350                1355                1360
Leu Glu Glu Pro Lys Asn Ser Thr Ile Glu Ala Leu Ile Ser Ile Asn
                    1365                1370                1375
Asn Gln Leu His Gln Thr Asp Ser Ala Ile Gly Ile Leu Lys His Ala
                    1380                1385                1390
```

```
Gln Gln His Asn Glu Leu Gln Leu Lys Glu Thr Trp Tyr Glu Lys Leu
        1395                1400                1405

Gln Arg Trp Glu Asp Ala Leu Ala Ala Tyr Asn Glu Lys Glu Ala Ala
    1410                1415                1420

Gly Glu Asp Ser Val Glu Val Met Met Gly Lys Leu Arg Ser Leu Tyr
1425                1430                1435                1440

Ala Leu Gly Glu Trp Glu Glu Leu Ser Lys Leu Ala Ser Glu Lys Trp
            1445                1450                1455

Gly Thr Ala Lys Pro Glu Val Lys Lys Ala Met Ala Pro Leu Ala Ala
                1460                1465                1470

Gly Ala Ala Trp Gly Leu Glu Gln Trp Asp Glu Ile Ala Gln Tyr Thr
        1475                1480                1485

Ser Val Met Lys Ser Gln Ser Pro Asp Lys Glu Phe Tyr Asp Ala Ile
    1490                1495                1500

Leu Cys Leu His Arg Asn Asn Phe Lys Lys Ala Glu Val His Ile Phe
1505                1510                1515                1520

Asn Ala Arg Asp Leu Leu Val Thr Glu Leu Ser Ala Leu Val Asn Glu
            1525                1530                1535

Ser Tyr Asn Arg Ala Tyr Asn Val Val Arg Ala Gln Ile Ile Ala
                1540                1545                1550

Glu Leu Glu Glu Ile Ile Lys Tyr Lys Lys Leu Pro Gln Asn Ser Asp
        1555                1560                1565

Lys Arg Leu Thr Met Arg Glu Thr Trp Asn Thr Arg Leu Leu Gly Cys
    1570                1575                1580

Gln Lys Asn Ile Asp Val Trp Gln Arg Ile Leu Arg Val Arg Ser Leu
1585                1590                1595                1600

Val Ile Lys Pro Lys Glu Asp Ala Gln Val Arg Ile Lys Phe Ala Asn
            1605                1610                1615

Leu Cys Arg Lys Ser Gly Arg Met Ala Leu Ala Lys Lys Val Leu Asn
                1620                1625                1630

Thr Leu Leu Glu Glu Thr Asp Asp Pro Asp His Pro Asn Thr Ala Lys
        1635                1640                1645

Ala Ser Pro Pro Val Val Tyr Ala Gln Leu Lys Tyr Leu Trp Ala Thr
    1650                1655                1660

Gly Leu Gln Asp Glu Ala Leu Lys Gln Leu Ile Asn Phe Thr Ser Arg
1665                1670                1675                1680

Met Ala His Asp Leu Gly Leu Asp Pro Asn Asn Met Ile Ala Gln Ser
            1685                1690                1695

Val Pro Gln Gln Ser Lys Arg Val Pro Arg His Val Glu Asp Tyr Thr
                1700                1705                1710

Lys Leu Leu Ala Arg Cys Phe Leu Lys Gln Gly Glu Trp Arg Val Cys
        1715                1720                1725

Leu Gln Pro Lys Trp Arg Leu Ser Asn Pro Asp Ser Ile Leu Gly Ser
    1730                1735                1740

Tyr Leu Leu Ala Thr His Phe Asp Asn Thr Trp Tyr Lys Ala Trp His
1745                1750                1755                1760

Asn Trp Ala Leu Ala Asn Phe Glu Val Ile Ser Met Leu Thr Ser Val
            1765                1770                1775

Ser Lys Lys Lys Gln Glu Gly Ser Asp Ala Ser Ser Val Thr Asp Ile
                1780                1785                1790

Asn Glu Phe Asp Asn Gly Met Ile Gly Val Asn Thr Phe Asp Ala Lys
        1795                1800                1805

Glu Val His Tyr Ser Ser Asn Leu Ile His Arg His Val Ile Pro Ala
```

```
            1810                1815                1820
Ile Lys Gly Phe Phe His Ser Ile Ser Leu Ser Glu Ser Ser Ser Leu
1825                1830                1835                1840

Gln Asp Ala Leu Arg Leu Leu Thr Leu Trp Phe Thr Phe Gly Gly Ile
                1845                1850                1855

Pro Glu Ala Thr Gln Ala Met His Glu Gly Phe Asn Leu Ile Gln Ile
                1860                1865                1870

Gly Thr Trp Leu Glu Val Leu Pro Gln Leu Ile Ser Arg Ile His Gln
                1875                1880                1885

Pro Asn Gln Ile Val Ser Arg Ser Leu Leu Ser Leu Leu Ser Asp Leu
                1890                1895                1900

Gly Lys Ala His Pro Gln Ala Leu Val Tyr Pro Leu Met Val Ala Ile
1905                1910                1915                1920

Lys Ser Glu Ser Leu Ser Arg Gln Lys Ala Ala Leu Ser Ile Ile Glu
                1925                1930                1935

Lys Met Arg Ile His Ser Pro Val Leu Val Asp Gln Ala Glu Leu Val
                1940                1945                1950

Ser His Glu Leu Ile Arg Met Ala Val Leu Trp His Glu Gln Trp Tyr
                1955                1960                1965

Glu Gly Leu Asp Asp Ala Ser Arg Gln Phe Phe Gly Glu His Asn Thr
1970                1975                1980

Glu Lys Met Phe Ala Ala Leu Glu Pro Leu Tyr Glu Met Leu Lys Arg
1985                1990                1995                2000

Gly Pro Glu Thr Leu Arg Glu Ile Ser Phe Gln Asn Ser Phe Gly Arg
                2005                2010                2015

Asp Leu Asn Asp Ala Tyr Glu Trp Leu Met Asn Tyr Lys Lys Ser Lys
                2020                2025                2030

Asp Val Ser Asn Leu Asn Gln Ala Trp Asp Ile Tyr Tyr Asn Val Phe
                2035                2040                2045

Arg Lys Ile Gly Lys Gln Leu Pro Gln Leu Gln Thr Leu Glu Leu Gln
                2050                2055                2060

His Val Ser Pro Lys Leu Leu Ser Ala His Asp Leu Glu Leu Ala Val
2065                2070                2075                2080

Pro Gly Thr Arg Ala Ser Gly Gly Lys Pro Ile Val Lys Ile Ser Lys
                2085                2090                2095

Phe Glu Pro Val Phe Ser Val Ile Ser Ser Lys Gln Arg Pro Arg Lys
                2100                2105                2110

Phe Cys Ile Lys Gly Ser Asp Gly Lys Asp Tyr Lys Tyr Val Leu Lys
                2115                2120                2125

Gly His Glu Asp Ile Arg Gln Asp Ser Leu Val Met Gln Leu Phe Gly
                2130                2135                2140

Leu Val Asn Thr Leu Leu Gln Asn Asp Ala Glu Cys Phe Arg Arg His
2145                2150                2155                2160

Leu Asp Ile Gln Gln Tyr Pro Ala Ile Pro Leu Ser Pro Lys Ser Gly
                2165                2170                2175

Leu Leu Gly Trp Val Pro Asn Ser Asp Thr Phe His Val Leu Ile Arg
                2180                2185                2190

Glu His Arg Glu Ala Lys Lys Ile Pro Leu Asn Ile Glu His Trp Val
                2195                2200                2205

Met Leu Gln Met Ala Pro Asp Tyr Asp Asn Leu Thr Leu Leu Gln Lys
                2210                2215                2220

Val Glu Val Phe Thr Tyr Ala Leu Asn Asn Thr Glu Gly Gln Asp Leu
2225                2230                2235                2240
```

Tyr Lys Val Leu Trp Leu Lys Ser Arg Ser Glu Thr Trp Leu Glu
            2245                2250                2255

Arg Arg Thr Thr Tyr Thr Arg Ser Leu Ala Val Met Ser Met Thr Gly
            2260                2265                2270

Tyr Ile Leu Gly Leu Gly Asp Arg His Pro Ser Asn Leu Met Leu Asp
            2275                2280                2285

Arg Ile Thr Gly Lys Val Ile His Ile Asp Phe Gly Asp Cys Phe Glu
        2290                2295                2300

Ala Ala Ile Leu Arg Glu Lys Phe Pro Glu Lys Val Pro Phe Arg Leu
2305                2310                2315                2320

Thr Arg Met Leu Thr Tyr Ala Met Glu Val Ser Gly Ile Glu Gly Ser
            2325                2330                2335

Phe Arg Ile Thr Cys Glu Asn Val Met Lys Val Leu Arg Asp Asn Lys
            2340                2345                2350

Gly Ser Leu Met Ala Ile Leu Glu Ala Phe Ala Phe Asp Pro Leu Ile
            2355                2360                2365

Asn Trp Gly Phe Asp Leu Pro Thr Lys Lys Ile Glu Glu Glu Thr Gly
            2370                2375                2380

Ile Gln Leu Pro Val Met Asn Ala Asn Glu Leu Leu Ser Asn Gly Ala
2385                2390                2395                2400

Ile Thr Glu Glu Glu Val Gln Arg Val Glu Asn His Lys Asn Ala
            2405                2410                2415

Ile Arg Asn Ala Arg Ala Met Leu Val Leu Lys Arg Ile Thr Asp Lys
            2420                2425                2430

Leu Thr Gly Asn Asp Ile Arg Arg Phe Asn Asp Leu Asp Val Pro Glu
            2435                2440                2445

Gln Val Asp Lys Leu Ile Gln Gln Ala Thr Ser Val Glu Asn Leu Cys
            2450                2455                2460

Gln His Tyr Ile Gly Trp Cys Pro Phe Trp
2465                2470

(2) INFORMATION FOR SEQ ID NO:4:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:4:

CCGGATCCCG TCGAGCTTCA GTTGAACTAC GGCGTGCTTC TGTAGCCATG GGAGTGCAGG        60

TGGA        64

(2) INFORMATION FOR SEQ ID NO:5:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

GGCCGGAATT CTCATTCCAG TTTTAGAA        28

(2) INFORMATION FOR SEQ ID NO:6:

(i) SEQUENCE CHARACTERISTICS:
        (A) LENGTH: 7 amino acids
        (B) TYPE: amino acid
        (D) TOPOLOGY: linear (ii) MOLECULE TYPE: DNA (genomic)

(xi) SEQUENCE DESCRIPTION: SEQ ID NO:6:

```
Thr Tyr Asp Pro Asn Gln Pro
 1               5
```

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:7:

```
His Ile Asp Phe Gly Asp
 1               5
```

(2) INFORMATION FOR SEQ ID NO:8:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (xi) SEQUENCE DESCRIPTION: SEQ ID NO:8:

```
Asn Asp Gln Val Phe Glu
 1               5
```

(2) INFORMATION FOR SEQ ID NO:9:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
GAGCCACCAC GATTTGCT                                              18
```

(2) INFORMATION FOR SEQ ID NO:10:

(i) SEQUENCE CHARACTERISTICS:
        (A) LENGTH: 64 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:10:

```
CCGGATCCCG TCGAGCTTCA GTTGAACTAC GGCGTGCTTC TGTAGCCATG GCGGCGGCCG    60

TTCC                                                                64
```

(2) INFORMATION FOR SEQ ID NO:11:

```
    (i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

GGCCGGAATT CTCAATCAAT ATCCACTA                                            28

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (xi) SEQUENCE DESCRIPTION: SEQ ID NO:12:

GGGGGATCCA CNTAYGAYCC NAAYCARC                                            28

(2) INFORMATION FOR SEQ ID NO:13:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

GCGGAATTCR TCNCCRAART CDATRTG                                             27

(2) INFORMATION FOR SEQ ID NO:14:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:14:

GGGGGATCCA AYGAYCARGT NTTYGA                                              26
```